(12) United States Patent
Haugland et al.

(10) Patent No.: US 7,816,527 B2
(45) Date of Patent: Oct. 19, 2010

(54) QUINAZOLINE-CONTAINING KITS FOR LABELING ALDEHYDE OR KETONE MOIETIES

(75) Inventors: Richard P. Haugland, Eugene, OR (US); Thomas H. Steinberg, Eugene, OR (US); Wayne F. Patton, Eugene, OR (US); Zhenjun Diwu, Sunnyvale, OR (US)

(73) Assignee: Life Technologies Corporation, Carlsbad, CA (US)

( * ) Notice: Subject to any disclaimer, the term of this patent is extended or adjusted under 35 U.S.C. 154(b) by 1311 days.

(21) Appl. No.: 11/182,122

(22) Filed: Jul. 15, 2005

(65) Prior Publication Data
US 2005/0250152 A1 Nov. 10, 2005

Related U.S. Application Data

(62) Division of application No. 09/970,215, filed on Oct. 2, 2001, now Pat. No. 6,967,251.

(60) Provisional application No. 60/237,932, filed on Oct. 2, 2000.

(51) Int. Cl.
*C07D 239/72* (2006.01)
(52) U.S. Cl. .................................. 544/287
(58) Field of Classification Search .......... 544/287
See application file for complete search history.

(56) References Cited

U.S. PATENT DOCUMENTS 5,316,906 A * 5/1994 Haugland et al. ............ 435/4

OTHER PUBLICATIONS

Garcia-Campaña, et al. J. Chromatogr. B, 793, 2003, pp. 49-74.*
Sauer, et al. J. Fluoresc. 3, 1993, pp. 131-139.*

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Dimitrova, et al. Dokladi na Bulgarskata Akademiya na Naukite, 51(9-10), 1998, 99-102 (Abstract only).*

* cited by examiner

Primary Examiner—James O Wilson
Assistant Examiner—Douglas M Willis

(57) ABSTRACT

Kits including novel fluorescent derivitization reagents for labeling an aldehyde- and/or ketone-containing target substance in a sample are described. In one embodiment kits are provided the novel fluorescent derivitization reagents of which have the following formula:

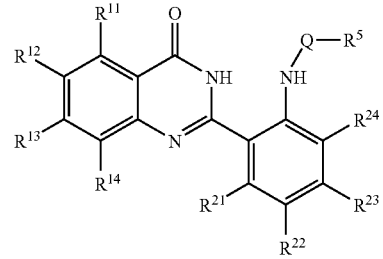

wherein Q is carbonyl, thiocarbonyl, or sulfonyl, and $R^5$ is -L-Z; L is arylene, or a $C_{1-6}$ perfluoroalkylene; Z is a carbonyl hydrazide, hydrazide, sulfonyl hydrazide, or a thiocarbonyl hydrazide; $R^{11}$-$R^{14}$ are independently H, $C_{1-16}$ alkyl, $C_{1-6}$ alkylamino, amino, or halogen; and $R^{21}$-$R^{24}$ are independently H, $C_{1-6}$ alkyl, $C_{1-6}$ alkoxy, $C_{1-6}$ perfluoroalkyl, $C_{1-6}$ alkylamino, di($C_{2-12}$-alkyl)amino, amino, carboxy, cyano, halogen, hydroxy, nitro, phenyl, sulfo, or -L-Z. The kits and reagents described are particularly useful for labeling glycoproteins or glycopeptides, nucleic acids, and lipopolysaccharides in electrophoresis gels.

14 Claims, 7 Drawing Sheets

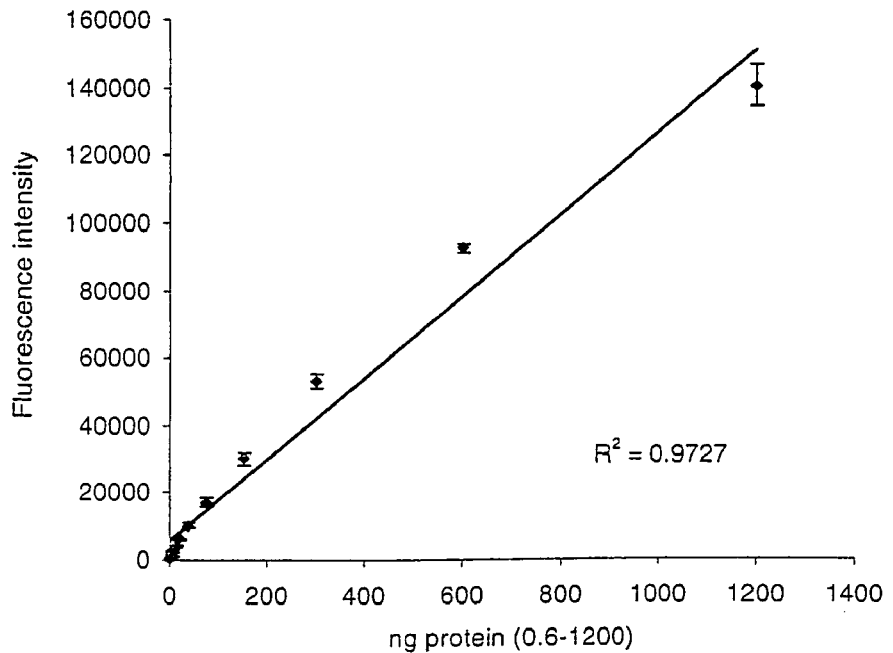
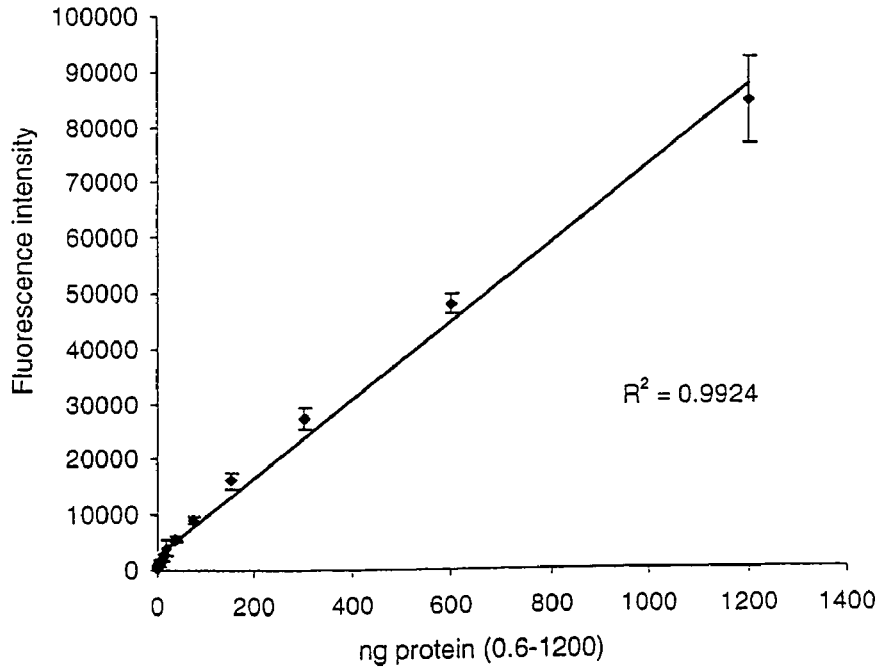

QUINAZOLINE-CONTAINING KITS FOR LABELING ALDEHYDE OR KETONE MOIETIES

CROSS-REFERENCE TO REALTED APPLICATIONS

This application is a division of U.S. Ser. No. 09/970,215, filed Oct. 2, 2001 now U.S. Pat. No. 6,967,251, which claims priority to U.S. Ser. No. 60/237,932, filed Oct. 2, 2000, which disclosures are herein incorporated by reference.

FIELD OF THE INVENTION

This invention relates to fluorescent derivatization reagents that label substances containing aldehydes, ketones, and similar functional groups, and their use in labeling glycoproteins and glycopeptides, nucleic acids and lipopolysaccharides, and other biomolecules.

BACKGROUND

Fluorescent dyes are known to be particularly suitable for biological applications in which a highly sensitive detection reagent is desirable. Fluorescent dyes are used to impart both visible color and fluorescence to other materials. Particularly useful are fluorescent reagents that exhibit selectivity in their labeling reactions, permitting the detection and/or identification of particular substances, or identification of characteristics of a sample.

A variety of detectable hydrazine, hydroxylamine and amine derivatives have been described that share the utility of labeling aldehyde and ketone functional groups. Among the most widely used of such reagents are dansyl hydrazine, fluorescein thiosemicarbazide, various biotin hydrazides, biotin hydroxylamine (ARP), and various aromatic amines (2-aminopyridine, 8-aminonaphthalene-1,3,6-disulfonic acid, 1-aminopyrene-3,6,8-trisulfonic acid, 2-aminoacridone) (as described by Haugland et al. MOLECULAR PROBES, INC. HANDBOOK OF FLUORESCENT PROBES AND RESEARCH CHEMICALS, $7^{TH}$ EDITION, on CD-ROM, Chapter 3, and references cited therein, which are incorporated by reference).

Most existing methods of labeling carbohydrates that utilize hydrazine, hydroxylamine and amine derivatization reagents have focused on labeling aldehydes present in, or introduced into, carbohydrates, particularly the so-called "reducing sugars". The adduct formed with the reducing sugar can be further stabilized by treatment with borohydride or a cyanoborohydride. The derivatization reaction typically proceeds or is followed by a separation technique such as chromatography, electrophoresis, precipitation, affinity isolation or other means before direct or indirect detection of the labeled product.

In addition, some simple and complex sugars have been derivatized by coupling to a carboxylic acid, as in glucuronides. Typically, the amine-, hydrazine- or hydroxylamine-substituted label functions as a nucleophile, and the carboxylic acid must first be activated by forming an ester or an anhydride, using an activating agent such as a carbodiimide (for example ethyldimethylaminopropyl carbodiimide, or EDAC). Capillary electrophoresis has been particularly effective for analysis of adducts or detectable derivatives with carbohydrates, including complex carbohydrates and carbohydrates obtained by hydrolysis of glycoproteins, gangliosides and other sugar-containing biomoleules. The detectable adducts thus formed in each case with the sugar or polysaccharide can themselves be utilized as tracers, for receptor binding, as enzyme substrates and for multiple other applications.

The derivatization reagents of this invention show fluorescence properties superior to those of any similar reagents that have been described for detection of aldehyde- or ketone-containing molecules in gels, and permit bright fluorescent labeling of carbohydrates, glycoproteins, glycogen, lipopolysaccharides, and other aldehyde, ketone, carboxylic acid, or sulfonic acid containing substances. Unlike biotin hydrazides, biotin hydroxylamines and digoxigenin hydrazides, all of which require blotting onto a membrane and the use of a secondary detection reagent, the reagents of the invention permit rapid detection of oxidized glycoproteins within gels.

The preferred reagents of the invention are well excited by ultraviolet excitation sources commonly used in epi-illuminators and transilluminators. The dyes possess unusually high Stokes shifts of greater than about 150 nm, effectively reducing background due to autofluorescence and scattering of the exciting light. In addition, the staining procedure of this invention is rapid and mild, exhibits substantially greater sensitivity than previously utilized labeling reagents, and employs a simple staining procedure.

A family of fluorogenic substrates that yield highly fluorescent products and that are related to the reagents of the invention has been previously described (U.S. Pat. No. 5,316,906 to Haugland et al. (1994); U.S. Pat. No. 5,443,986 to Haugland et al. (1995); both incorporated by reference). However, these known fluorogenic substrates are nonfluorescent until enzyme action, are not substituted by a reactive functional group to label a desired target substance, and their fluorescent products are designed to be insoluble under physiological conditions. In contrast, in preferred embodiments of the invention, the non-fluorescent reagents only become fluorescent when bound to the biomolecules with aldehyde or ketone moieties, e.g. in a gel or on a membrane.

BRIEF DESCRIPTION OF THE DRAWINGS

FIG. 3: Sensitivity and linear dynamic range of glycoprotein detection after SDS-polyacrylamide gel electrophoresis and staining with Compound 5. (A.) α1-acid glycoprotein (B.) avidin. α1-Acid glycoprotein is a glycoprotein containing 40% carbohydrate while avidin is a glycoprotein containing 10% carbohydrate. 1 ng or less of each glycoprotein can be detected and the linear dynamic range of detection exceeds 3 orders of magnitude. Conventional periodic acid Schiff's (PAS) detection using acid Fuchsin sulfite permits detection of only 38 ng of glycoprotein with a linear dynamic range of only 30-fold.

SUMMARY OF THE INVENTION AND DESCRIPTION OF THE PREFERRED EMBODIMENTS

Figure 1:
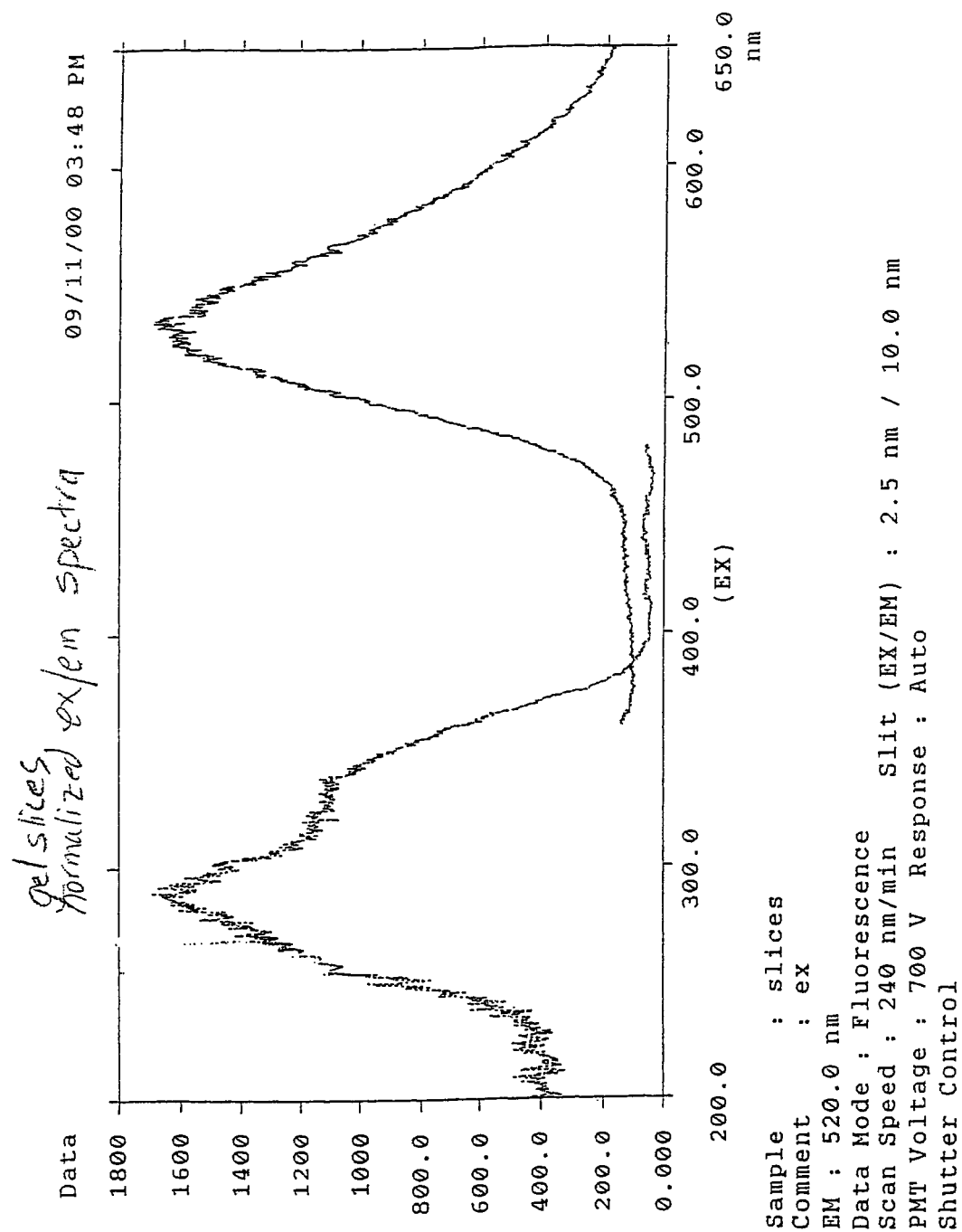
FIG. 1: Fluorescence excitation/emission spectra for Compound 5-labeled α1-acid glycoprotein. Approximately 7.5 µg of protein was loaded onto a 13% SDS-polyacrylamide gel and subjected to electrophoresis by standard procedures. After labeling with Compound 5 (as described in Example 19), the resulting fluorescent band was excised and placed in a 2 mm×10 mm quartz cuvette. The large Stoke's shift of Compound 5 is spectrally separable from the blue fluorescence emission of plastic backings commonly used as supports for pre-cast polyacrylamide gels, and is spectrally separable from emission of red-fluorescent protein stains, allowing multicolor detection of glycosylated and unglycosylated proteins in gels and on blots.
Figure 2A:
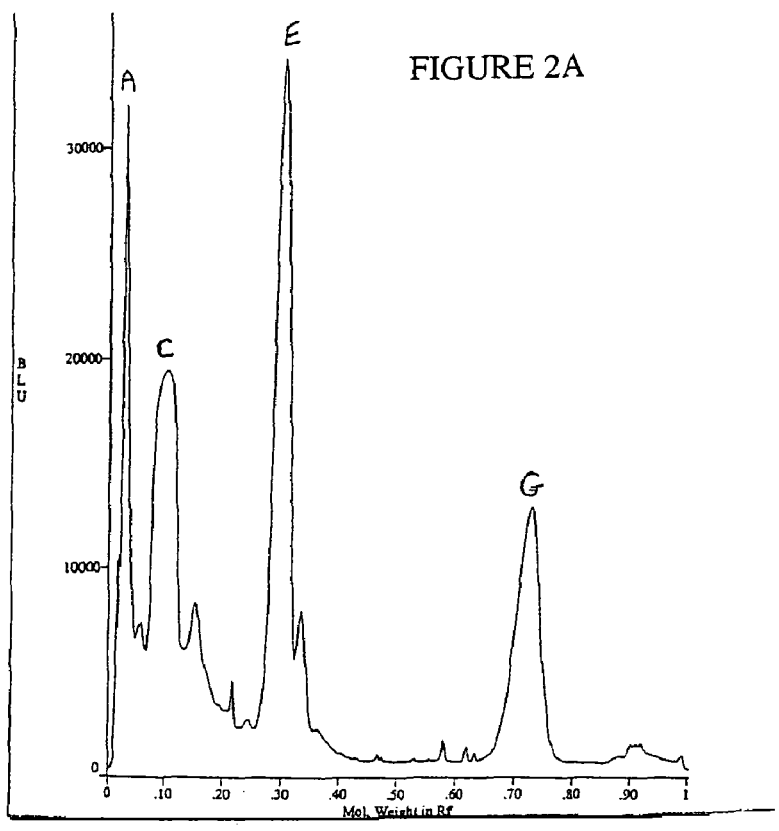
FIG. 2: Intensity profiles of a protein mixture separated by SDS polyacrylamide gel electrophoresis and either labeled with Compound 5 or with a nonspecific total protein stain (SYPRO RUBY protein gel stain). (A.) Labeling of glycoproteins with Compound 5. (B.) Staining of proteins with SYPRO RUBY protein gel stain. The proteins evaluated are: A) α2-macroglobulin (180 kDa, glycosylated), B) phosphorylase b (97 kDa, nonglycosylated), C) glucose oxidase (82 kDa, glycosylated), D) bovine serum albumin (66 kDa, nonglycosylated), E) α1-acid glycoprotein (42 kDa, glycosylated), F) carbonic anhydrase (29 kDa, nonglycosylated), G) avidin (8 kDa, glycosylated), H) lysozyme (14 kDa, nonglycosylated). Glycoproteins may be selectively labeled directly in gels using Compound 5, with minimal nonspecific staining of nonglycosylated proteins.
Figure 2B:
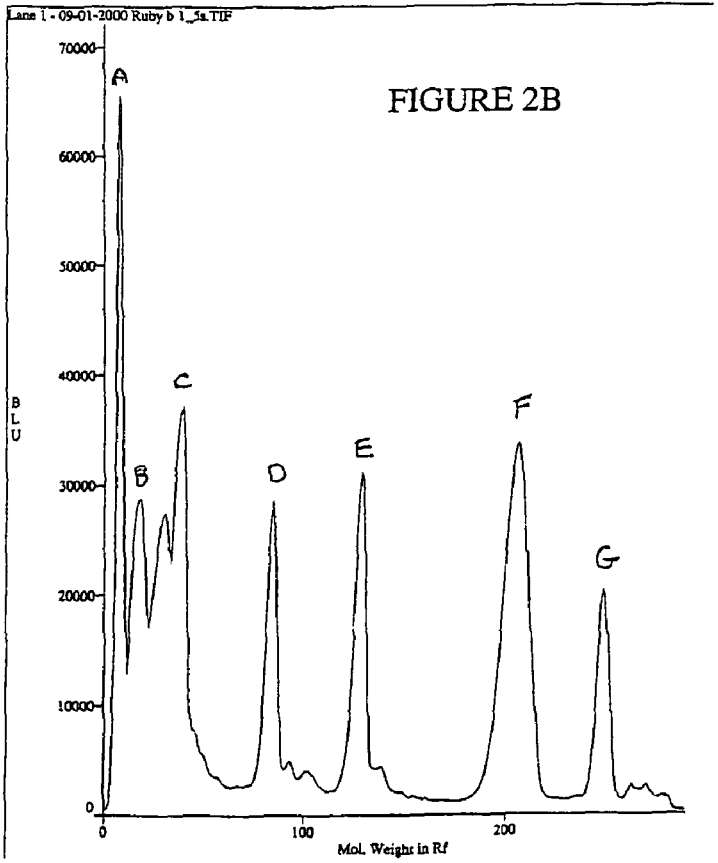
Figure 4:
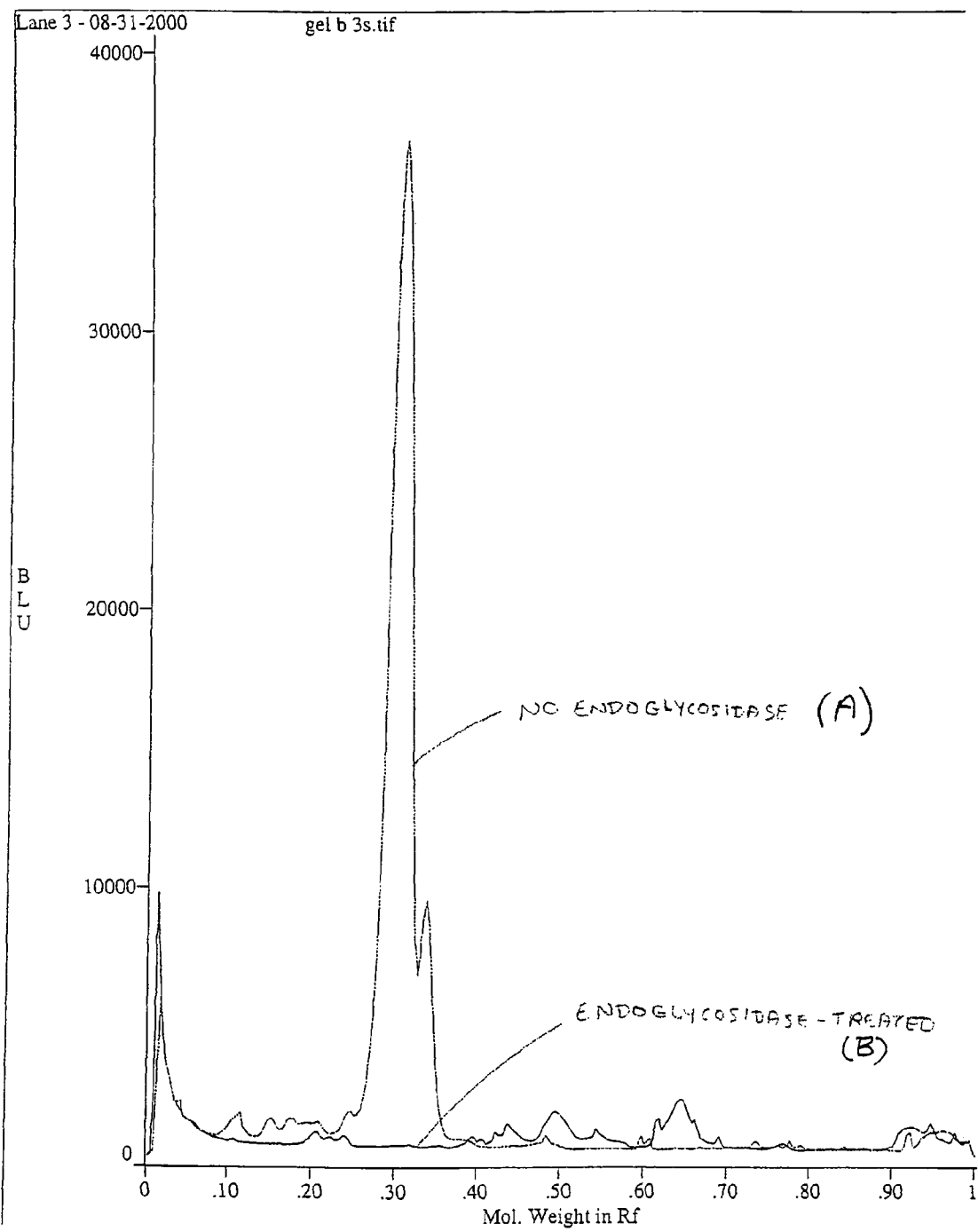
FIG. 4: Mobility shift analysis of protein deglycosylation as detected using Compound 5: (A.) Line trace of the electrophoretic profile of α1-acid glycoprotein prior to treatment with endoglycosidases. (B.) Line trace of the electrophoretic profile of the same protein after exposure to endoglycosidases. Enzymatic removal of the carbohydrate residues from the glycoprotein results in a loss of staining using Compound 5, thus demonstrating the specificity of detection for carbohydrates in the presence of proteins.
Figure 5:
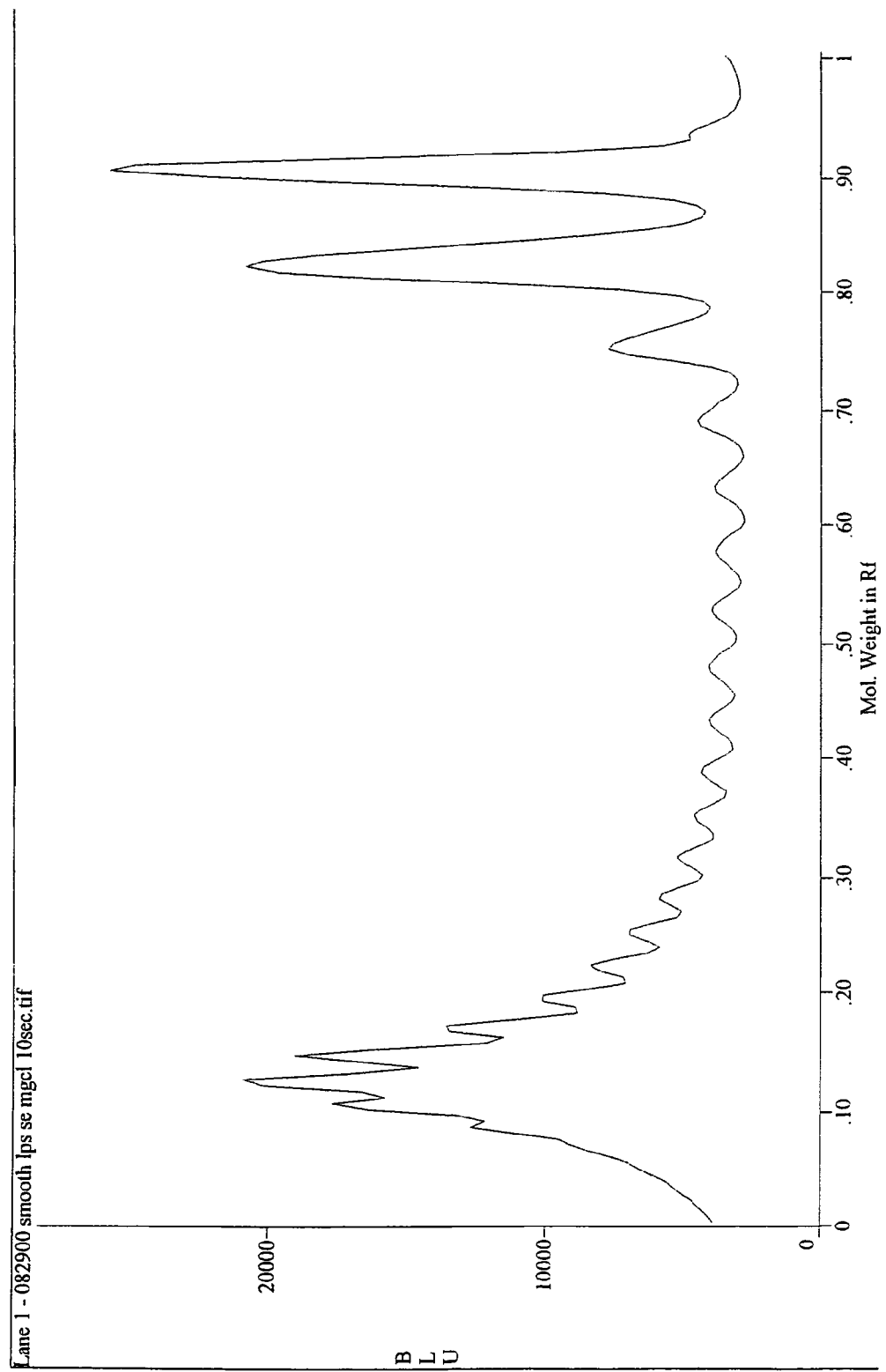
FIG. 5: Intensity profile of electrophoretically separated *Escherichia coli* serotype 055:B5 lipopolysaccharide detected with Compound 5. The reagents of the invention represent a substantial improvement over previously published lipopolysaccharide staining methods, such as silver staining or zinc-imidazole reverse staining of gels (requiring 200 to 1000 ng of lipopolysaccharide) or digoxigenin hydrazide-based immunoblotting procedures (requiring 30 ng of lipopolysaccharide).
Figure 6:
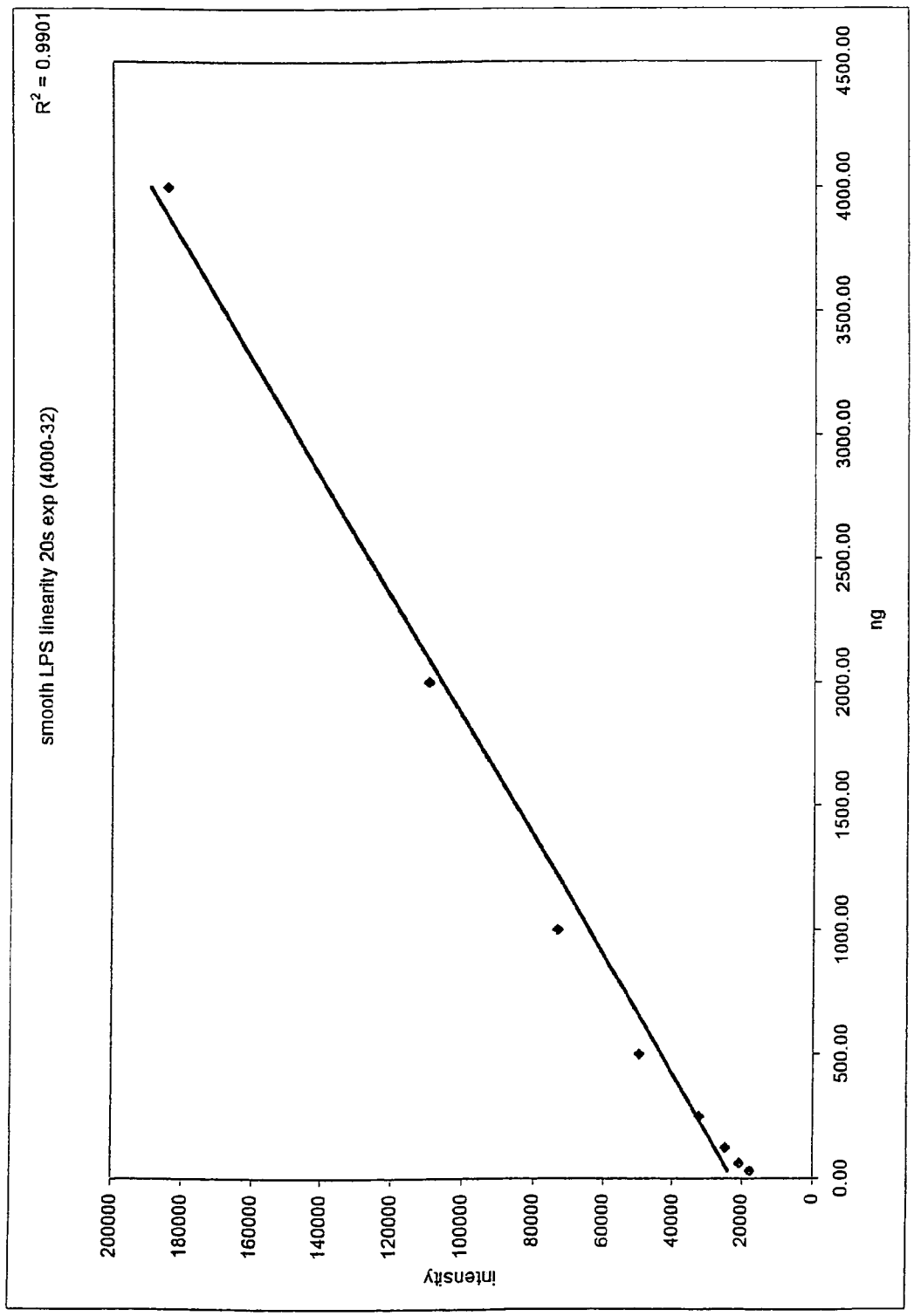
FIG. 6: Sensitivity and linear dynamic range of lipopolysaccharide detection after SDS-polyacrylamide gel electrophoresis. Detection is linear from 2 ng to 4000 ng ($R^2$=0.9901), exceeding the sensitivity of most common gel-based and blot-based methods of lipopolysaccharide detection by 15-500 fold. The linear dynamic range of detection is similarly improved over standard methods, extending over 3-orders of magnitude compared to the 10-30 fold range for other methods.

This invention describes novel fluorescent derivatization reagents suitable for coupling to target substances that contain aldehydes, ketones, carboxylic acids and sulfonic acids, thereby conferring their chromophoric and fluorescence properties onto the conjugated substance.

The reagents of the invention are substituted by at least one reactive group (Z) that is a hydrazide or a hydroxylamine, that is bound to the aromatic portion of the reagent by a covalent linkage L.

The derivatization reagents of the invention have the formula:

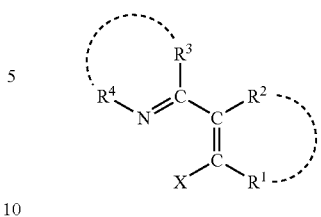

where the substituents $R^1$ and $R^2$, when taken in combination, form a first aromatic ring system. The first aromatic ring system comprises a 5- or 6-membered aromatic ring that optionally incorporates one or more heteroatoms N, O, or S. The first aromatic ring system optionally incorporates 1 or 2 additional fused aromatic rings that each optionally incorporate one or more heteroatoms. The first aromatic ring system is optionally substituted by halogen, alkyl having 1-6 carbons, perfluoroalkyl having 1-6 carbons, alkoxy having 1-6 carbons, sulfo, carboxy, hydroxy, amino, alkylamino having 1-6 carbons, dialkylamino having 2-12 carbons, nitro, cyano, aryl, or any combination thereof, or the first aromatic ring system is substituted by a covalently bound reactive group -L-Z. Typical nonhydrogen substituents on the first aromatic ring system are halogen or alkoxy. Where the reagent is substituted by halogen, it is typically substituted by F, Cl or Br. Typically, the first aromatic ring system is a benzene or naphthalene that is optionally substituted as above. Preferably, the first aromatic ring system is a benzene that is substituted once by -L-Z.

The substituents $R^3$ and $R^4$, when taken in combination, form a second aromatic ring system. The second aromatic ring system comprises a 5- or 6-membered aromatic ring that optionally incorporates 1-3 additional heteroatoms N, O, or S, or oxo, thiooxo, sulfone, or amino functionalities. The second aromatic ring optionally incorporates 1 or 2 additional fused aromatic rings that themselves optionally incorporate one or more heteroatoms. The second aromatic ring system is optionally substituted by halogen, alkyl having 1-6 carbons, perfluoroalkyl having 1-6 carbons, alkoxy having 1-6 carbons, sulfo, carboxy, hydroxy, amino, alkylamino having 1-6 carbons, dialkylamino having 2-12 carbons, nitro, cyano, aryl, or any combination thereof, or the second aromatic ring system is substituted by a covalently bound reactive group -L-Z. Typical nonhydrogen substituents on the first aromatic ring system are halogen or alkoxy. Where the reagent is substituted by halogen, it is typically substituted by F, Cl or Br. Typically the second aromatic ring incorporates two fused rings. In one aspect of the invention, the second aromatic ring system is a quinazolinone, or a benzazole. In another aspect of the invention, the second aromatic ring system is a benzoxazole, a benzothiazole, or an indoline ring system.

In one embodiment, $R^2$ and $R^3$, when taken in combination, form an additional 5- or 6-membered ring that is doubly fused to the first and second aromatic ring systems. In this embodiment, the bridge connecting the first ring system to the second ring system comprises a combination of saturated or unsaturated carbon-carbon bonds, O, N, or S atoms. The carbon and nitrogen atoms of the bridging moiety are optionally substituted by alkyl having 1-6 carbons or by the reactive group -L-Z.

Preferably, the reagents of the invention comprise at least three aromatic rings, two of which are fused. Typically either the first ring system or the second ring system consists of two fused rings. Typically, the bridging moiety is not present.

The X moiety is OH or —NH-Q-$R^5$, where the Q moiety is an electron-withdrawing linking group. Any stable divalent radical that is sufficiently electronegative is a suitable Q moiety. In one aspect of the invention, the Q moiety has a Hammett sigma constant more positive than 0.20. In a particular aspect, the Q moiety is carbonyl (—(C═O)—), thiocarbonyl (—(C═S)—), sulfonyl (—(SO$_2$)—), or phosphoryl (—(PO$_2$)—). In a preferred aspect of the invention, Q is carbonyl, thiocarbonyl or sulfonyl.

$R^5$ is alkyl having 1-6 carbons, alkoxy having 1-6 carbons, alkylamino having 1-6 carbons, or $R^5$ is the reactive group -L-Z. Preferably, X is —N-Q-$R^5$ and $R^5$ is -L-Z.

Z is a functional group capable of reacting with an aldehyde or ketone to form a covalent bond. In one aspect of the invention, Z is an aliphatic or aromatic amine, such as ethylenediamine, or an amine covalently bound directly to the first or second aromatic ring system. In another embodiment Z is —NR$^6$—NH$_2$ (hydrazide), —NR$^6$(C═O)NR$^7$NH$_2$ (semicarbazide), —NR$^6$(C═S)N R$^7$NH$_2$ (thiosemicarbazide), —(C═O)NR$^6$NH$_2$ (carbonylhydrazide), —(C═S)NR$^6$NH$_2$ (thiocarbonylhydrazide), —(SO$_2$)NR$^6$NH$_2$ (sulfonylhydrazide), —NR$^6$NR$^7$(C═O)NR$^8$NH$_2$ (carbazide), —NR$^6$NR$^7$(C═S)NR$^8$N H$_2$ (thiocarbazide), or —O—NH$_2$ (hydroxylamine), where each $R^6$, $R^7$, and $R^8$ is independently H, or alkyl having 1-6 carbons, preferably H. In one aspect of the invention, Z is a hydrazide, hydroxylamine, carbohydrazide or a sulfonylhydrazide. Preferably, Z is a carbohydrazide or a sulfonylhydrazide.

The covalent linkage L binds Z to the fluorophore, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, phosphorus-oxygen bonds, and phosphorus-nitrogen bonds. L typically includes ether, thioether, carboxamide, sulfonamide, urea, urethane or hydrazine moieties.

Preferred L moieties have 1-20 nonhydrogen atoms selected from the group consisting of C, N, O, P, and S; and are composed of any combination of ether, thioether, amine, ester, carboxamide, sulfonamide, hydrazide bonds and aromatic or heteroaromatic bonds. Preferably L is a combination of single carbon-carbon bonds that optionally includes one or two heteroatoms, or L comprises an aromatic ring. Examples of L include substituted or unsubstituted polymethylene, arylene, alkylarylene, arylenealkyl, or arylthio. In one embodiment, L contains 1-6 carbon atoms; in another, L contains a thioether linkage.

Although the reagents of the invention may be substituted by more than one -L-Z moiety, they must be substituted by at least one -L-Z moiety. Preferably, the reagent of the invention is substituted by only one -L-Z moiety, and more preferably $R^5$ is the only -L-Z moiety (bound to the reagent at Q).

The preferred reagents of the invention exhibit an excitation maximum greater than about 250 nm, and a Stokes shift of the emission greater than about 100 nm, more preferably greater than about 150 nm In one embodiment of the invention, the fluorophore has the structure

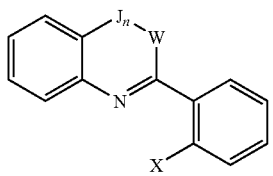

where W is (CH$_3$)$_2$C (isopropylidene), —CH═(methine), —CH$_2$—, S, O, or —(N—R$^9$)— wherein $R^9$ is H or alkyl having 1-6 carbons. J is —(C═O)—, —(SO$_2$)—, or —CH═; and n is 1 or 0. When W is —(N—R$^9$)— and J is —(C═O)—, the products are quinazolinones (also referred to as quinazolones). When W is —(N—R$^9$)— and J is absent (n=0), the product are benzimidazoles. When W is S and J is absent (n=0), the products are benzothiazoles. When W is O and J is absent (n=0), the products are benzoxazoles. When W and J are each methine, the products are quinolines. When W is isopropylidene and J is absent (n=0), the products are indolines.

When the first aromatic ring and the second aromatic ring are both 6-membered rings, and the bridging moiety forms a 5- or 6-membered ring between them, the products are phenanthridines. Typically, where the reagent of the invention is a phenanthridine, it has the structure:

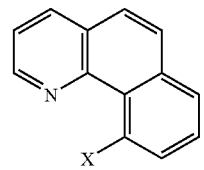

In another aspect of the invention, the reagent of the invention is a quinazolinone, a benzimidazole, a benzothiazole, a benzoxazole, a quinoline, an indoline, or a phenanthridine that is independently substituted one or more times by F, Cl, Br, $C_1$-$C_6$ alkyl, $C_1$-$C_6$ perfluoroalkyl, $C_1$-$C_6$ alkoxy, nitro, cyano, or aryl, or any combinations thereof.

In yet another aspect of the invention, the reagent of the invention is structurally similar to a quinazolinone, a benzimidazole, a benzothiazole, a benzoxazole, a quinoline or an indoline but is further modified in that at least one of the aromatic rings is fused to at least one additional aromatic ring that optionally incorporates at least one hetero atom N, O, or S.

For use in detecting glycoproteins or glycopeptides, nucleic acids, and lipopolysaccharides, the preferred reagent of the invention has the formula:

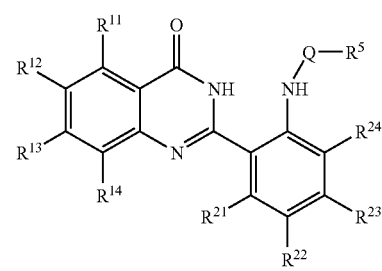

Formula XXX wherein Q is carbonyl, thiocarbonyl, or sulfonyl, preferably sulfonyl, and $R^5$ is -L-Z. Typically, L is arylene (preferably phenylene), a perfluoroalkyl (preferably $C_{3-6}$), or a single covalent bond; and Z is a carbonyl hydrazide, hydrazide, sulfonyl hyrdrazide, or a thiocarbonyl hydrazide. The substituents $R^{11}$-$R^{14}$ are independently H, $C_{1-6}$ alkyl, $C_{1-6}$ alkoxy, $C_{1-6}$ perfluoroalkyl, $C_{1-6}$ alklyamino, $C_{2-12}$ dialkylamino, amino, carboxy, cyano, halogen, hydroxy, nitro, phenyl, or sulfo. Typically, $R^{11}$-$R^{14}$ are H, or only one of $R^{11}$-$R^{14}$ is non-hydrogen, which non-hydrogen substituent is preferably F, Cl, Br, or alkoxy. The substituents $R^{21}$-$R^{24}$ are independently H, $C_{1-6}$ alkyl, $C_{1-6}$ alkoxy, $C_{1-6}$ perfluoroalkyl, $C_{1-6}$ alklyamino, $C_{2-12}$ dialkylamino, amino, carboxy, cyano, halogen, hydroxy, nitro, phenyl, sulfo, or -L-Z. Typically, $R^{21}$-$R^{24}$ are H, or only one of $R^{21}$-$R^{24}$ is non-hydrogen (preferably $R^{22}$), which non-hydrogen substituent is preferably F, Cl, Br, sulfo, or L-Z.

Reagent-Target Conjugates

The product of cross-coupling with a target substance that contains an aldehyde, ketone, carboxylic acid, or sulfonic acid functionality is a reagent-target conjugate. In the reagent-target conjugates, the fluorophore is bound to the target substance (ST) by a covalent linkage, L'.

The nature of the linkage, L', is distinct from the linkage L that originally bound the reactive Z moiety to the reagent of the invention. L' typically comprises the original L linkage, and also incorporates the atoms originally present in the Z moiety and the functional group conjugated thereto. Typical linkages with aldehydes or ketones incorporate an oxime, an amide, a hydrazone, a carbohydrazone, a thiocarbohydrazone, a sufonylhydrazone, a semicarbazone, a thiosemicarbazone, or similar functionality reflecting the specific nature of the reactive group Z used and the aldehyde or ketone conjugated therewith. Linkages with carboxylic acids are typically referred to as carbohydrazides or as hydroxamic acids. Linkages with sulfonic acids are typically referred to as sulfonylhydrazides or N-sulfonylhydroxylamines. The linkage L' may be formed completely by the conjugation reaction between the reagent and the target, or may be subsequently stabilized by chemical reduction.

The aldehyde or ketone functional group is typically naturally present on the target substance prior to its conjugation to the reagent of the invention. Alternatively, the aldehyde or ketone functionality is formed on the target substance by chemical, light, heat, radiation, or enzymatic treatment prior to reaction with a reagent of the invention. In one aspect of the invention, the target substance is treated with an oxidizing condition, such as a chemical oxidizing agent (for example a periodate, a strong acid, or ozone), oxidizing radiation, photolysis, or enzymatic oxidation. Carboxylic and sulfonic acid functionalities are typically already present in the target substance, but may require special conditions for coupling to the reagents of the invention.

Although a variety of chemical oxidants such as dichromate and permanganate are effective at oxidizing simple and complex alcohols to aldehydes or ketones, they can be harsh reagents when used with biomolecules and may overoxidize alcohols to carboxylic acids, which do not couple without use of an auxiliary coupling agent such as EDAC. More commonly the oxidizing agent is one that oxidizes vicinal glycols or aminoalcohols. By far the most common reagent of this type is periodic acid ($HIO_4$) or one of its salts such as sodium periodate. Oxidation by periodates is gentle and highly selective. The product(s) of the reaction typically contain two aldehyde moieties, although ketones are also formed from appropriately substituted glycols. Some examples of molecules that contain periodate-oxidizable glycols that can subsequently be derivatized by the reagents of the invention include monosaccharides, disaccharides and polysaccharides; the 5'-terminal nucleotide in ribonucleic acids; serine, threonine and unblocked peptides and proteins that contain terminal serine or threonine residues; transfer ribonucleic acids loaded with serine or threonine; ethylene glycol, glycerol, glycerol 1-phosphate, 2-aminoalcohols and similar derivatives; many glycoproteins, including immunoglobulins, peroxidase, avidin; various glycolipids, glycosphingolipids, gangliosides and lipopolysaccharides; and numerous conjugates of drugs, ligands and natural products that contain periodate-oxidizable glycol or aminoalcohol functional groups.

An additional method for selective derivatization (and subsequent detection) of certain carbohydrates, for example galactosides, is through the enzyme-catalyzed oxidation of the carbohydrate to an aldehyde, which can be subsequently reacted with a detectable amine, hydrazine or hydroxylamine derivative. This treatment is primarily effective for carbohydrates in which catalytic oxidation yields an aldehyde, such as galactose residues. Glucose oxidase, for instance, does not yield an aldehyde when it oxidizes glucosides. An application of this reaction is the highly selective modification and identification of cell-surface galactoside-containing proteins in live cells using galactose oxidase.

Certain other molecules have intrinsic aldehydes or ketones that react with detectable amines, hydrazines or hydroxylamines spontaneously or with moderate warming at an appropriate pH. In addition to reducing sugars and some oligosaccharides, in which the aldehyde (or ketone) is predominantly in a ring structure, these reactions have frequently been used for derivatization of low molecular weight molecules such as drugs and hormones (e.g. steroids) and other ligands that have molecular weights <2000, most often followed by separation from excess reagent and analysis by a chromatographic technique such as thin layer chromatography, HPLC or electrophoresis. Only a few proteins, such as elastin, collagen, and substrates of lysyl oxidase, have intrinsic aldehyde or ketone functional groups, which permit their selective detection in the presence of other proteins without an oxidation step. Some additional natural products that can be derivatized include, but are not limited to, acetaldehyde, glyceraldehyde, dihydroxyacetone, and pyruvates.

An extremely wide variety of carboxylic acids are derivatized by the reagents of the invention, in conjunction with carboxylate-activating reagents. Suitable carboxylic acids include $C_1$ to $C_{30}$ carboxylic acids that are linear, branched, saturated or unsaturated or that contain additional aliphatic or aromatic rings or additional substituents; intermediates in the citric acid cycle; synthetic polymers (including carboxylate-modified microspheres and membranes); amine-blocked amino acids, peptides and proteins; drugs; ligands of MW <2000; and selected polysaccharides. Sulfonyl halides (expecially sulfonyl chlorides) are readily coupled to amines, hydrazines and hydroxylamines of the invention, to form stable sulfonamides.

The reagents of the invention can label nucleotides, oligonucleotides and nucleic acids by multiple means, including 1) periodate oxidation of the 5'-terminus of ribonucleic acids followed by coupling to a Z moiety that is an amine or a hydrazine; 2) coupling to cytosine residues mediated by bisulfite; 3) the Feulgen reaction, in which a deoxynucleoside, a deoxynucleotide, or an oligodeoxynucleotide of a DNA is treated with acid to yield a hemiacetal that is then coupled with a reagent of the invention.

Abasic sites of nucleic acids (formed by radiation exposure, reactive oxygen treatment and certain other chemical treatments), lack their bases and comprise the same hemiacetal link that is formed by the Feulgen reaction. Thus these abasic sites are also detected with the reagents of the instant invention.

With the exception of some steroids, cellular lipids typically do not contain aldehyde or ketone moieties. These are typically introduced by oxidation of alcohols or hydroperoxides. Carbon-carbon double bonds are converted to glycols using a reagent such as osmium tetroxide, and are then oxidized to aldehydes by a periodate. It is more common to detect lipid conjugates of sugars, such as lipopolysaccharides (LPS), gangliosides, cerebrosides and glycosylsphingolipids by periodate oxidation of their carbohydrate portion to aldehydes. The reagents of this invention provide exceptionally sensitive detection of oxidized LPS (Example 26).

Where they are not present, aldehydes and ketones are also introduced into molecules using extrinsic reagents that already contain an aldehyde or ketone. For instance, aldehydes are introduced at aliphatic amine sites with the reagents succinimidyl 4-formylbenzoate or succinimidyl 4-formylphenoxyacetate (Molecular Probes, Eugene Oreg.). These reagents selectively modify proteins on the surface of live cells, and thereby permit the analysis of the topology of peptide and protein exposure on cells surfaces following, for instance, lysis and gel electrophoresis. Additionally, galactosides are enzymatically transferred to a target carbohydrate using UDP-galactose:N-acetylglucosamine galactosyltransferase and, following galactose oxidase-catalyzed oxidation to an aldehyde (as described by Shaper et al. J. SUPRAMOL. STRUCTURE 6, 291-299 (1977)), the target carbohydrate can be modified by a reagent of the invention. Glycoproteins such as horseradish peroxidase are oxidized to aldehydes and their conjugates subsequently used in various detection schemes according to the instant invention (Example 28).

The oligosaccharide components of cell surface glycoproteins play a role in the interactions that regulate many important biological processes, from cell-cell adhesion to signal transduction. Sialic acids are the most abundant terminal components of oligosaccharides on mammalian cell-surface glycoproteins and are synthesized from the six-carbon precursor N-actylmannosamine. When cells in culture are incubated with N-levulinoyl-D-mannosamine, this ketone-containing monosaccharide serves as a substrate in the oligosaccharide synthesis pathway, resulting in ketone-tagged cell-surface oligosaccharides (as described in U.S. Pat. No. 6,075,134 to Bertozzi et al. (2000), incorporated by reference). If these tagged cells are then labeled with a reagent of the invention, they are readily identified or traced using either by imaging or flow cytometry.

The conjugated target is typically a peptide, a protein, a nucleoside, a nucleotide, an oligonucleotide, a nucleic acid, a sugar, a polysaccharide, a lipid, a lipopolysaccharide, a ganglioside, a drug, a hormone, or a ligand having a molecular weight less than 2,000 Daltons. Preferably, the conjugated target is a protein, a nucleic acid, a lipid, a lipopolysaccharide, a ganglioside, a drug, or a hormone. Most preferably, the conjugated target is a glycoprotein, a lipopolysaccharide, or a nucleic acid.

Methods of Use

The use of the invention to label aldehyde- and ketone-containing target substances comprises combining a reagent of the present invention with a sample that contains or is thought to contain a desired target, incubating the mixture of reagent and sample for a time sufficient for the reagent to form a covalent conjugate with the target substance in the sample, such that the conjugate exhibits a detectable fluorescent signal. Conjugation of the instant reagents with carboxylic acid- and sulfonic acid-containing substances requires prior activation of these functional groups to an amine-reactive species.

The characteristics of the resulting reagent-target conjugate, including the presence, location, intensity, excitation and emission spectra, fluorescence polarization, fluorescence lifetime, photobleaching rate and other physical properties of the fluorescent signal can be used to detect, differentiate, sort, quantitate, and/or analyze aspects or portions of the sample. The reagents of the invention are optionally used in conjunction with one or more additional detection reagents (preferably having detectably different fluorescence characteristics).

Selected Target Substances Containing Aldehydes or Ketones
Formaldehyde
Acetone
Benzaldehydes
Reducing sugars and polysaccharides in ring-opened forms
Steroids
Keto acids
Aldehyde- or ketone-containing drugs
Aldehyde- or ketone-containing environmental pollutants
Aldehyde- or ketone-containing organics
Acid-treated deoxyribonucleic acids
Oxidized sugars
Oxidized polysaccharides
Oxidized glycols
Oxidized glycoproteins
Oxidized glycolipids
Oxidized glycosaminoglycans
Oxidized ribonucleic acids
Oxidized biological cells
Oxidized N-terminal serine residues of proteins
Oxidized N-terminal threonine residues of proteins Selected Target Substances Containing Carboxylic Acids or Sulfonic Acids
Steroids
Carboxylic acids
carboxylic or sulfonic acid-containing drugs
carboxylic or sulfonic acid-containing environmental pollutants
carboxylic or sulfonic acid-containing organics
fatty acids
carboxylated sugars
polymers
biological cells
proteins Staining Solution Typically, when the reagent of the invention is used to detect aldehydes or ketones, it is used in the form of a staining solution, preferably an aqueous or aqueous miscible solution that is compatible with the sample and the intended use. For biological samples, where minimal perturbation of cell morphology or physiology is desired, the staining solution is selected accordingly. For solution assays, the staining solution preferably does not perturb the native conformation of the target substance.

Although typically used in an aqueous or aqueous miscible solution, the staining solution is typically prepared by first dissolving the reagent in a water-miscible organic solvent such as dimethylsulfoxide (DMSO), dimethylformamide (DMF), or a lower alcohol, such as methanol or ethanol. This stock solution is typically prepared at a concentration of greater than about 50-times that used in the final staining solution, then diluted one or more times with an aqueous solvent or a buffer solution such that the reagent is present in an effective amount. Typically, the reagent is first dissolved in 100% DMF, and then diluted with buffer. The staining solution optionally further comprises additional formulation components, such as acids, buffering agents, inorganic salts, polar organic solvents, antioxidants, and ion chelators.

The pH of the staining solution is optionally modified by the inclusion of a buffering agent. Any buffering agent that is compatible with the target substance in the sample is suitable for inclusion in the staining solution.

In one embodiment, the buffering agent is one of the so-called "Good's" buffers. "Good's" buffers include BES (N,N-bis[2-hydroxyethyl]-2-aminoethanesulfonic acid; 2-[bis(2-hydroxyethyl)amino]ethanesulfonic acid), BICINE (N,N-bis[2-hydroxyethyl]glycine), CAPS (3-[cyclohexylamino]-1-propanesulfonic acid), EPPS(N-[2-hydroxyethyl] piperazine-N'-[3-propanesulfonic acid]), HEPES ((N-[2-hydroxyethyl]piperazine-N'-[2-ethanesulfonic acid]), MES (2-[N-morpholino]ethanesulfonic acid), MOPS (3-[N-morpholino]propanesulfonic acid), PIPES (piperazine-N,N'-bis[2-ethanesulfonic acid]; 1,4-piperazinediethanesulfonic acid), TAPS(N-tris[hydroxymethyl]methyl-3-aminopropanesulfonic acid; ([2-hydroxy-1,1-bis(hydroxymethyl) ethyl]amino-1-propanesulfonic acid), TES (N-tris[hydroxymethyl]methyl-2-aminoethanesulfonic acid; 2-([2-hydroxy-1,1-bis(hydroxymethyl)ethyl]amino) ethanesulfonic acid), or TRICINE (N-tris[hydroxymethyl] methylglycine; N-[2-hydroxy-1,1-bis(hydroxymethyl)ethyl] glycine).

Other preferred buffering agents include salts of formate, citrate, acetate, N-(2-hydroxyethyl)-N'-(2-sulfoethyl)piperazine, imidazole, N-(2-hydroxyethylpiperazine)-N'-2-ethanesulfonic acid, Tris(hydroxymethyl)aminomethane acetate, or Tris (hydroxymethyl)aminomethane hydrochloride. In a preferred embodiment, the buffering agent is MES, sodium acetate, or acetic acid, preferably acetic acid. The buffering agent or mixture of buffering agents is typically present in the staining solution at a concentration of 20 mM to 500 mM, preferably about 25 mM to about 100 mM. Where the buffering agent is acetic acid, it is preferably present in a concentration of about 1%-6%, more preferably at about 3%.

In a particularly advantageous formulation of the staining solution, the staining solution additionally comprises an inorganic salt. Advantageous inorganic salts produce staining formulations that exhibit low background signals when staining glycoproteins in electrophoretic gels. Particularly useful and inexpensive salts include sodium chloride, ammonium sulfate, magnesium chloride, magnesium acetate, zinc chloride, magnesium sulfate and magnesium glucuronate present in the staining solution at a concentration of 1-50%. In a preferred embodiment, the inorganic salt is sodium chloride or magnesium chloride, more preferably magnesium chloride.

An effective amount of reagent is the amount of reagent sufficient to give a detectable fluorescence response in combination with the desired target. The reagent concentration in the solution must be sufficient both to contact the target in the sample and to combine with the target in an amount sufficient to give a signal, but too much reagent may cause problems with background fluorescence or speckling in gels. The optimal concentration and composition of the staining solution is determined by the nature of the sample (including physical, biological, biochemical and physiological properties), the nature of the reagent-target interaction (including the transport rate of the reagent to the site of the target), and the nature of the analysis being performed, and can be determined using standard procedures, similar to those described in examples below.

Where the target substance contains a carboxylic acid or sulfonic acid functional group, the functional group must first be activated before combining with a staining solution containing a reagent of the invention, depending upon the properties of the target substance. Typically carbodiimides, such as EDAC, or dicyclohexylcarbodiimide (DCC) are used to activate carboxylic acids, whereas sulfonic acids most often require formation of their sulfonyl chloride by standard means. The reagent adducts of carboxylic acids and sulfonic acids are typically used to characterize the target substance, or the conjugates are used as fluorescent tracers. Carboxylic acid and sulfonic acids do not form stable adducts when stained in gels or solutions, thus differentiating them from aldehydes and ketones.

In one embodiment of the staining solution, the compound has the formula of Formula XXX described above. In a preferred embodiment, the staining solution contains a compound selected from the group consisting of Compounds 5, 20, 21, and 23 described below; more preferably Compounds 5, 20, and 23.

Sample Types

The target of interest is optionally enclosed within a biological structure (i.e. an organism or a discrete unit of an organism), free in solution (including solutions that contain biological structures), immobilized in or on a solid or semi-solid material, or is extracted from a biological structure (e.g. from lysed cells, tissues, organisms or organelles).

In one aspect of the invention, the target is a biological structure and is optionally a cell or tissue. Typically, the sample containing the desired target is an aqueous or aqueous miscible solution that is obtained directly from a liquid source or as a wash from a solid material (organic or inorganic) or a growth medium or a buffer solution in which biological structures have been placed for evaluation.

In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuffs, such as meat, grain, produce, eggs, or dairy products.

In yet another embodiment, the sample is a solid or semi-solid matrix and the target of interest is present on or in the matrix. In one aspect of the invention, the matrix is a membrane. In another aspect, the matrix is an electrophoretic gel, such as is used for separation and characterization of proteins or nucleic acids. In another aspect, the matrix is a silicon chip, a glass fiber, or glass slide, and the target of interest has been immobilized on the chip, fiber, or slide, such as in an array. In yet another aspect, the matrix is a polymeric microparticle, and the target has been immobilized on the surface of the microparticle.

The source and type of sample, as well as the use of the reagent, will determine which reagent characteristics, and thus which reagents, will be most useful for staining a particular sample. Where the fluorescence of the reagent-target complex or reagent conjugate is detected utilizing sustained high intensity illumination (e.g. microscopy), reagents with a rate of photobleaching lower than commonly used reagents (e.g. fluorescein) are preferred, particularly for use in live cells. Where the reagent must penetrate cell membranes or a gel, more permeant reagents are preferred. Reagents that rapidly and readily penetrate cell membranes do not necessarily rapidly penetrate gels.

In one aspect of the invention, the sample is also exposed to an oxidizing condition, such as a strong acid (the Feulgen reaction), oxidizing radiation, oxidizing enzymes, and chemical oxidizing agents. The sample is typically exposed to an oxidizing condition by combining the sample with an oxidizing agent. Typically the oxidizing agent is added to the sample before combination with the staining solution. In one aspect of the invention, the oxidizing agent is a depurinating agent that generates an aldehyde on a nucleic acid. Preferably the depurinating agent is HCl. In another aspect of the invention, the oxidizing agent is a periodate.

Formation of the Reagent-Target Complex

The sample is combined with the staining solution by any means that facilitates contact between the reagent and the target. The contact may occur through simple mixing, as in the case where the sample is a solution. Alternatively, the staining solution is added to the sample and the resulting combined mixture is incubated for a time sufficient to form the reagent-target conjugate. A staining solution may contact the target in a liquid separation medium such as an electrophoretic liquid, sieving matrix or running buffer, or in a chemically compatible sedimentation or buoyant density gradient (e.g. containing CsCl), or on an inert matrix, such as a blot or gel, a testing strip, or any other solid or semi-solid support. Suitable supports also include, but are not limited to, polymeric microparticles (including paramagnetic microparticles), polyacrylamide and agarose gels, nitrocellulose filters, optical fibers, computer chips (such as silicon chips), natural and synthetic membranes, liposomes and chemically compatible hydrogels, and glass (including optical filters), and other silica-based and plastic support. The reagent is optionally combined with the sample prior to undergoing gel or capillary electrophoresis, gradient centrifugation, or other separation step, during separation, or after the sample undergoes separation. Alternatively, the reagent is combined with an inert matrix or solution in a capillary prior to addition of the sample, as in pre-cast gels, capillary electrophoresis or preformed density or sedimentation gradients. Alternatively, formation of the reagent-target conjugate occurs in a medium such as is used for an organic synthesis.

Where the target is enclosed in a biological structure, the sample is typically incubated with the reagent. While some reagents may permeate biological structures rapidly and completely upon addition of the reagent solution, any other technique that is suitable for transporting the reagent into the biological structure is also a valid method of combining the sample with the subject reagent. Some cells actively transport the reagents across cell membranes (e.g. endocytosis or ingestion by an organism or other uptake mechanism) regardless of their cell membrane permeability. Suitable artificial means for transporting the reagents across cell membranes include, but are not limited to, action of chemical agents such as detergents, enzymes or adenosine triphosphate; receptor- or transport protein-mediated uptake; liposomes or alginate hydrogels; phagocytosis; pore-forming proteins; microinjection; electroporation; hypo-osmotic shock; or minimal physical disruption such as scrape loading, patch clamp methods, or bombardment with solid particles coated with or in the presence of the reagents. Preferably, where intact structures are desired, the methods for staining cause minimal disruption of the viability of the cell and integrity of cell or intracellular membranes. Alternatively, the cells are fixed and treated with routine histochemical or cytochemical procedures, particularly where pathogenic organisms are suspected to be present. It should be well-understood that aldehyde fixatives such as acrolein or glutaraldehyde should be avoided, as even after fixation they maintain a free aldehyde group that will cross-react with the reagents of the invention. However, the method of the invention is compatible with paraffin-embedded tissues, and fixation schemes such as 10% buffered formalin.

The sample is combined with the reagent for a time sufficient to form the fluorescent reagent-target conjugate. Where the target is present in a gel or on a blot, sample is combined with the reagent for the time required to give a high signal-to-background ratio after washing. Optimal staining with a particular reagent is dependent upon the physical and chemical nature of the individual sample and the sample medium, as well as the property being assessed. The optimal time is usually the minimum time required for the reagent, in the concentration being used, to achieve the highest target-specific signal while avoiding degradation of the sample over time and minimizing all other fluorescent signals due to the reagent. Where the reagent of the invention is used synthetically as a derivatization reagent, the optimal time for mixing is typically the minimum time required to form the highest yield of the covalent adduct, as determined by experimentation. A preferred yield is a quantitative formation of the covalent adduct.

Preferably, when used with biological specimens, the reagent is combined with the sample at a temperature optimal for biological activity of the target within the operating parameters of the reagents (usually between 0 °C and 60 °C, with reduced stability of the reagents at higher temperatures). For in vitro assays, the reagent is typically combined with the sample at about room temperature (23 °C).

The method of the instant invention is useful for labeling target molecules in a variety of applications, including electrophoretic gels; thin layer chromatograms; targets present on blots, chips, strips and other surfaces; targets present in flowing systems, such as in flow cytometry, HPLC, capillary electrophoresis, and microfluidic devices; and in solution in multiwell plates, facilitating high throughput screening by automated methods. In some cases the target substance is labeled with the reagent of the invention prior to a separation technique. Alternatively, target substances are first separated, as in electrophoretic gels or on surfaces, prior to labeling with the reagents of the invention.

Additional Reagents

The method of the present invention optionally further comprises one or more additional reagents that are simultaneously or sequentially combined with the sample mixture, the staining solution, or the combined mixture. An additional reagent is optionally a detection reagent that colocalizes with the target or other analyte to enhance the detection thereof. The additional reagent is optionally selected to be useful for identification of other components or characteristics of the sample mixture, such as a poly(amino acid) stain, nucleic acid stain, a stain for lipids or carbohydrates, or a pH indicator. Alternatively, the additional reagent is a detection reagent designed to interact with a specific portion of the sample mixture, so as to probe for a specific component of the sample mixture (such as an antibody or antibody conjugate), where spatial coincidence of the reagent-target conjugate and the detection reagent indicates that the additional reagent is also associated with the target.

The additional reagent also incorporates a means for producing a detectable response. A detectable response means a change in, or occurrence of, a parameter in a test system that is capable of being perceived, either by direct observation or instrumentally. Such detectable responses typically include the change in, or appearance of, color, fluorescence, reflectance, pH, chemiluminescence, infrared spectra, magnetic properties, radioactivity, light scattering, x-ray scattering, or the precipitation of an electron-rich product. Appropriate means to provide a detectable response include, but are not limited to, a visible or fluorescent dye, a chemiluminescent reagent, an enzyme substrate that produces a visible or fluorescent precipitate upon enzyme action (for example, the action of horseradish peroxidase upon diaminobenzidine, or enzyme action on a labeled tyramide), visible- or fluorescent-labeled microparticles, a metal such as colloidal gold, or a silver-containing reagent, or a signal that is released by the action of light upon the reagent (e.g. a caged fluorophore that is activated by photolysis, or the action of light upon diaminobenzidine), or a radioactive signal. The detectable signal of the additional reagent is detected simultaneously or sequentially with the optical signal of the conjugates of the present invention.

In one embodiment of the invention, the additional detection reagent is selected to exhibit overlapping spectral characteristics, such that energy transfer occurs between the reagent-target conjugate and the detection reagent, resulting in labeled targets that exhibit an extended Stokes shift. Alternatively, the additional detection reagent colocalizes with the reagent-target conjugate such that the labeling of some or all targets exhibit quenching.

One class of useful additional detection reagents are fluorescent nucleic acid stains. A variety of appropriate nucleic acid stains are known in the art, including but not limited to, thiazole orange, ethidium homodimer, ethidium bromide, propidium iodide, Hoechst 33258, and DAPI. Additional useful nucleic acid stains are described in the international applications WO 93/06482, DIMERS OF UNSYMMETRICAL CYANINE DYES (published Apr. 1, 1993) or WO 94/24213, CYCLIC SUBSTITUTED UNSYMMETRICAL CYANINE DYES (published Oct. 27, 1994); U.S. Pat. No. 5,321,130 to Yue et al., 1994; or U.S. Pat. No. 5,410,030 to Yue et al., 1995 (all incorporated by reference). The use of an appropriate nucleic acid stain in conjunction with the reagents of the present invention permits simultaneous or sequential observation of the desired target and nucleic acids such as DNA and RNA.

Another class of useful additional detection reagents are fluorescent protein stains. A variety of appropriate protein stains are known in the art, including but not limited to, those described in the international application WO 00/25139, LUMINESCENT PROTEIN STAINS AND THEIR METHOD OF USE (published May 4, 2000), or U.S. Pat. No. 5,616,502 to Haugland et al., 1997; incorporated by reference. Selected preferred fluorescent protein stains are sold under the trademarks SYPRO RED, SYPRO ORANGE, SYPRO ROSE, SYPRO ROSE PLUS, and SYPRO RUBY by Molecular Probes, Inc. (Eugene, Oreg.). The use of an appropriate protein stain in conjunction with the reagents of the present invention permits simultaneous or sequential observation of the desired target and total protein present in the sample.

An additional class of useful additional detection reagents are fluorescent-labeled antibodies, lectins or avidins, in particular those that are labeled with an OREGON GREEN dye or ALEXA FLUOR dye, commercially available from MOLECULAR PROBES, INC., Eugene, Oreg.

In one embodiment, the additional reagent comprises a member of a specific binding pair having a detectable label. Representative specific binding pairs are shown in Table 1.

TABLE 1

Representative specific binding pairs

| | |
|---|---|
| enzyme | enzyme substrate |
| antigen | antibody |
| biotin | avidin (or streptavidin) |
| IgG* | protein A or protein G |
| carbohydrate | lectin |
| nucleic acid aptamer | protein |

*IgG is an immunoglobulin

The additional detection reagent is used in conjunction with enzyme conjugates to localize the detectable response of the additional reagent. Enzyme-mediated techniques take advantage of the attraction between specific binding pairs to detect a variety of analytes. In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

Additional classes of preferred detection reagents include labeled antibodies, ion indicators (including $Na^+$ indicators, $Ca^{2+}$ indicators, or pH indicators), organelle stains, cell viability indicators, or chemically reactive dyes.

Illumination and Observation

At any time after or during staining, the sample is illuminated with a wavelength of light capable of exciting the reagent to produce a detectable optical response, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The presence of the optical response is optionally used to identify the presence of the analyte in the test sample. Alternatively, the detectable optical response is quantified and used to measure the concentration of the target in the sample mixture. Quantification is typically performed by comparison of the optical response to a prepared standard or to a calibration curve. Typically, the measured optical response is compared with that obtained from a standard dilution of a known concentration of the target in an electrophoretic gel, or on a membrane. Generally a standard curve must be prepared whenever an accurate measurement is desired. Alternatively, the standard curve is generated by comparison with a reference dye or dyed particle that has been standardized versus the reagent-target conjugate desired.

In one aspect of the invention, stained electrophoretic gels are used to analyze the composition of complex sample mixtures and additionally to determine the relative amount of a particular target in such mixtures.

Comparison/Differentiation Assays

The method of the invention further comprises assays wherein two samples, or two aliquots of the same sample, are each treated with a reagent of the invention and the optical response of each sample and/or aliquot is then compared.

In one aspect of the method, each aliquot is from the same original sample, but one aliquot is treated with a reagent or exposed to a condition, while the other is used as a control. In another aspect of the method, each sample has a different composition, and the samples are compared after both are treated with a reagent of the invention. In a further aspect of the invention, the sample is polydisperse, as in the case of cells and tissues, and the targets are spatially resolved. The samples are optionally exposed to an oxidizing condition, treated with an acid or an enzyme prior to adding a staining solution. In addition, each sample is optionally subjected to a separation step before or after treatment with a staining solution.

Selected embodiments of this method include:
  Comparing the electrophoretic mobility of the components of two treated samples to highlight differences in the samples.
  Distinguishing between Gram-positive and Gram-negative bacteria by detecting the lipooligosaccharides expressed on the surface of mucosal Gram-negative bacteria (see Example 26).
  Comparing a sample treated with a glycosidase enzyme with an appropriate negative control.
  Comparing proteins treated with galactose oxidase with an appropriate negative control.
  Comparing cells treated with functionalized glycoconjugates with an appropriate negative control.
  Differentiating cells based on DNA content (after treatment by the Feulgen reaction).
  Differentiating cell surface proteins that have been subjected to an oxidizing condition from internal proteins that have not been oxidized.
  Differentiating normal and tumor cells.
  Differentiating glycosylated albumins from nonglycosylated albumins
  differentiating types of blood cells by differences in carbohydrate content, optionally using flow cytometry Kits Due to the simplicity of use of the instant reagents, they are particularly useful in the formulation of a kit for the labeling of selected targets, comprising one or more reagents (preferably in a stock solution), instructions for the use of the reagent to label or detect a desired target, and optionally comprising target standards and other components (such as inorganic salts, buffers, or wash solutions). In one embodiment, the kit of the invention comprises a stock solution of a reagent of the invention and one or more additional kit components.

The additional kit components may be selected from, without limitation, acids, buffering agents, inorganic salts, polar solvents, and positive and negative controls. The additional kit components are present as pure compositions, or as aqueous solutions that incorporate one or more additional kit components. Any or all of the kit components optionally further comprise buffers. Where the additional kit component is an inorganic salt, it is typically a sodium or magnesium salt.

In one aspect of the invention, the kit contains an oxidizing agent (preferably a periodate salt), a stock solution of a reagent of the invention in an organic solvent, a buffer solution that additionally comprises an inorganic salt, molecular weight standards, and optionally an additional detection reagent that is a fluorescent total protein stain. Preferably, the compound in the staining solution is Formula XXX. In another aspect of the invention, the staining solution in the kit contains Compound 5, 20, 21, or 23; preferably 5, 20 or 23.

The examples below are given so as to illustrate the practice of this invention. They are not intended to limit or define the entire scope of this invention.

EXAMPLE 1

Preparation of Compound 1

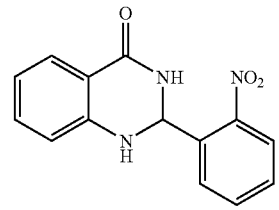

Anthranilamide (0.2 mol) and 2-nitrobenzaldehyde (0.22 mol) are dissolved in anhydrous ethanol (EtOH, 1 L). To the EtOH solution is added p-toluenesulfonic acid monohydrate (TsOH, 0.01 mol). The reaction mixture is stirred at room temperature for 2 h, and then refluxed until anthranilamide is completely consumed. The reaction mixture is cooled to room temperature, and directly used for the next step reaction without further purification.

EXAMPLE 2

Preparation of Compound 2

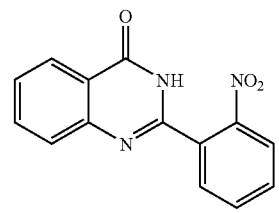

To the solution of crude Compound 1 prepared in Example 1 (0.2 mol) is slowly added 2,3-dichloro-5,6-dicyano-1,4-quinone (DDQ, 0.21 mol) at room temperature. The reaction mixture is stirred at room temperature until Compound 1 is completely consumed. The reaction mixture is concentrated in vacuo, and filtered to collect the resulting precipitate. The crude solid is washed with cold 1:1 EtOH/benzene until the residual DDQ and 2,3-dichloro-5,6-dicyano-1,4-dihydroquinone are completely removed. The crude material is further recrystallized (from EtOH/ethyl ether) to give the desired product (51 g).

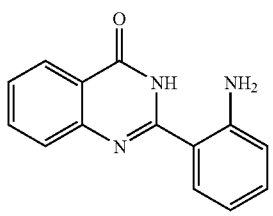

EXAMPLE 3

Preparation of Compound 3

To a solution of Compound 2 (0.1 mol) in tetrahydrofuran (500 mL) is slowly added tin (II) chloride (0.5 mol) at room temperature. The reaction mixture is heated at 50-60° C. until compound 2 is completely consumed. The solution is carefully poured onto crushed ice/2 M HCl, and filtered to collect the resulting solid. The crude solid is suspended in water, and neutralized with $NaHCO_3$ to pH 8.0-9.0. The resulting suspension is filtered to collect the solid. The crude material is washed with water, dried and recrystallized to give the desired product (24 g).

EXAMPLE 4

Preparation of Compound 4

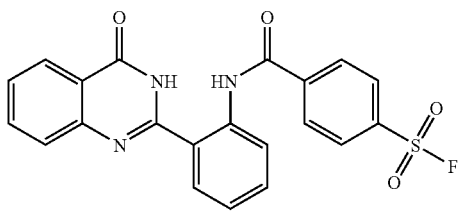

To a solution of Compound 3 (10 mmol) in N,N-dimethylformamide (DMF, 50 mL) is slowly added 4-fluorosulfonylbenzoyl chloride (11 mmol) at room temperature. The reaction mixture is stirred at room temperature until Compound 3 is completely consumed. The solution is then carefully poured onto crushed ice/water, and filtered to collect the resulting solid. The crude solid is redissolved in DMF, and precipitated with ethyl ether. The solubilization/precipitation process is repeated twice to give the desired product (3.8 g).

EXAMPLE 5

Preparation of Compound 5

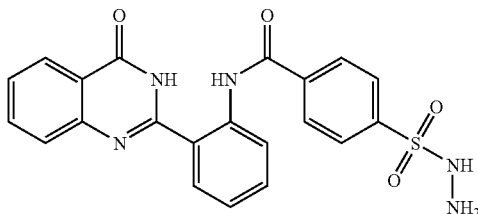

To a methanol solution of anhydrous hydrazine (50 mmol, 5 mL) is slowly added a DMF solution of Compound 4 (5 mmol, 5 mL). The reaction mixture is stirred at room temperature until Compound 4 is completely consumed. The solution is concentrated in vacuo, poured into water, and filtered to collect the resulting solid. The crude solid is redissolved in DMF, and precipitated with water. The solubilization/precipitation process is repeated until the residual hydrazine is completely removed (TLC detection by ninhydrin spraying). The crude material is recrystallized from EtOH to give the desired product which has yellow/green fluorescence (1.8 g).

EXAMPLE 6

Preparation of Compound 6

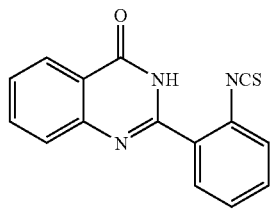

To a THF suspension of Compound 3 (0.5 mmol, 5 mL) is slowly added thiophosgene (5 mmol, 5 mL). The reaction mixture is heated at reflux until Compound 3 is completely consumed. The resulting solution is evaporated in vacuo, and the residue is washed with ether. The crude solid is directly used for the next step reaction without further purification.

EXAMPLE 7

Preparation of Compound 7

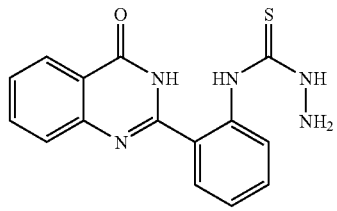

To a DMF solution of anhydrous hydrazine (5 mmol, 0.5 mL) is slowly added a DMF solution of Compound 6 (0.5 mmol, 0.5 mL). The reaction mixture is stirred at room temperature until Compound 6 is completely consumed. The solution is poured into water, and filtered to collect the resulting solid. The crude solid is redissolved in DMF, and precipitated with water. The solubilization/precipitation process is repeated until the residual hydrazine is completely removed. The crude material is recrystallized from EtOH to give the desired product, which has blue fluorescence (1.8 g).

EXAMPLE 8

Preparation of Compound 8

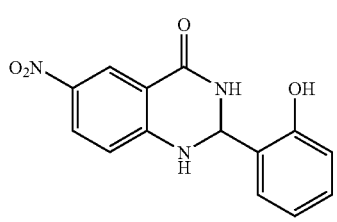

Compound 8 is prepared analogously to Compound 1 using 5-nitroanthranilamide and salicylaldehyde.

EXAMPLE 9

Preparation of Compound 9

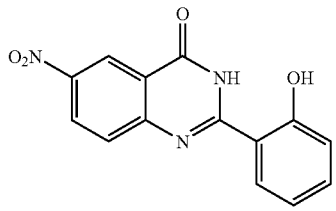

Compound 9 is prepared by oxidation of Compound 8 as in the procedure of Compound 2.

EXAMPLE 10

Preparation of Compound 10

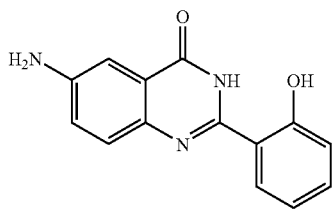

Compound 10 is prepared by reduction of Compound 8 as in the procedure of Compound 3. Compound 10 exhibits green fluorescence.

EXAMPLE 11

Preparation of Compound 11

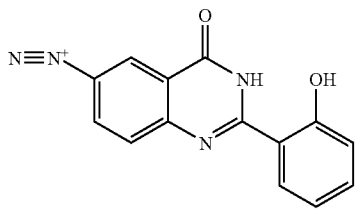

To a cold suspension of Compound 10 (0.1 mmol) in concentrated hydrochloric acid (10 mL) is slowly added 95% $NaNO_2$ (0.11) while maintaining the reaction temperature at 0-5° C. The reaction mixture is stirred at room temperature until Compound 10 is completely consumed. The reaction mixture is checked with starch-iodide paper for excess nitrous acid, which is then destroyed by adding small quantities of urea. The resulting solution is directly used in the next reaction.

EXAMPLE 12

Preparation of Compound 12

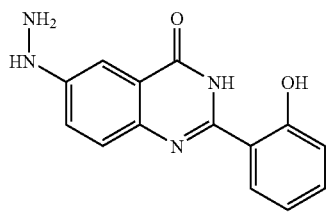

To the solution of crude Compound 11 prepared above (0.1 mol) is slowly added 5 M aqueous tin (II) chloride (0.3 mol, in concentrated HCl) at room temperature. The reaction mixture is stirred at room temperature until compound 11 is completely consumed. The reaction mixture is diluted with water, and filtered to yield the resulting precipitate, which is repeatedly washed with water to remove the residual tin chloride. The resulting solid is suspended in water, and neutralized with $NaHCO_3$ (pH 7.0-7.5). The mixture is filtered to collect the precipitate that is further washed with water. The solid is dried, and recrystallized from EtOH to give the desired product, which has green fluorescence (67 mg).

EXAMPLE 13

Preparation of Compound 13

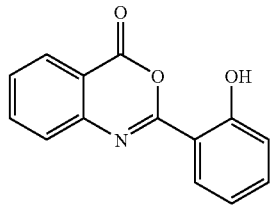

Anthranilic acid (10 mmol) and 2-hydroxybenzaldehyde (12 mmol) are dissolved in polyphosphoric acid (10 mL). The reaction mixture is heated at 60-70° C. for 4-6 h. The solution is then cooled to room temperature, and poured into ice/water. The resulting precipitate is collected by filtration, and washed with water. The crude material is further purified on a silica gel column eluting with 5:1 chloroform/ethyl acetate to give the desired product (1.2 g).

EXAMPLE 14

Preparation of Compound 14

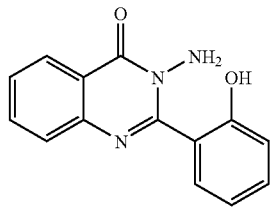

To a methanol solution of anhydrous hydrazine (5 mmol, 5 mL) is slowly added a methanol solution of Compound 13 (1 mmol, 5 mL). The reaction mixture is then heated to 50-60° C. until Compound 13 is completely consumed. The solution is then concentrated in vacuo, poured into water, and filtered to collect the resulting solid. The crude solid is dissolved in DMF, and precipitated with water. The solubilization/precipitation process is repeated until the residual hydrazine is completely removed. The crude material is recrystallized from ethyl acetate to give the desired product, which has blue fluorescence (1.8 g).

EXAMPLE 15

Preparation of Compound 15

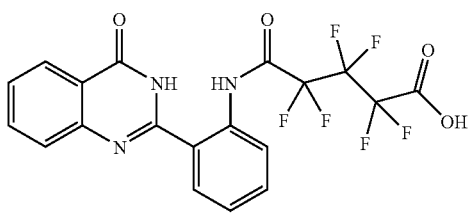

Compound 15 is prepared as in the procedure for Compound 4 using Compound 3 and hexafluoroglutaric anhydride.

EXAMPLE 16

Preparation of Compound 16

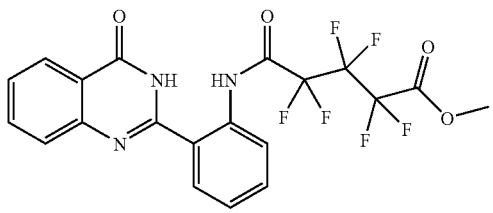

To a methanol solution of Compound 15 (1 mmol, 25 mL MeOH) is added 0.1 mL concentrated sulfuric acid. The reaction mixture is heated at 50-60° C. until Compound 15 is completely consumed. The resulting solution is concentrated in vacuo, poured into water, and filtered to collect the resulting solid. The crude solid is washed with water until pH 6.0-7.0, and purified on a silica gel column, eluting with a gradient mixture of chloroform/methanol.

EXAMPLE 17

Preparation of Compound 17

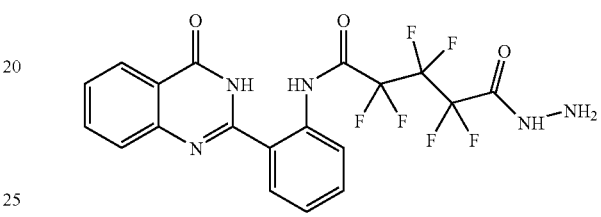

To a methanol solution of anhydrous hydrazine (5 mmol, 5 mL) is slowly added a methanol solution of Compound 16 (1 mmol, 5 mL). The reaction mixture is stirred at room temperature until Compound 16 is completely consumed. The resulting solution is concentrated in vacuo, poured into water, and filtered to collect the resulting solid. The crude solid is redissolved in methanol, and precipitated with water. The solubilization/precipitation process is repeated until the residual hydrazine is completely removed. The crude material is recrystallized from ethyl acetate to give the desired product, which exhibits green fluorescence (213 mg).

EXAMPLE 18

Preparation of Compounds 20-34

Compounds 20-34 are prepared according to the procedures indicated in Table 2.

TABLE 2

| Compound | Prepared as in Example: | Fluorescence color |
|---|---|---|
| ![Compound 20 structure]<br>Compound 20 | 4 | yellow |

TABLE 2-continued
| Compound | Prepared as in Example: | Fluorescence color |
|---|---|---|
| 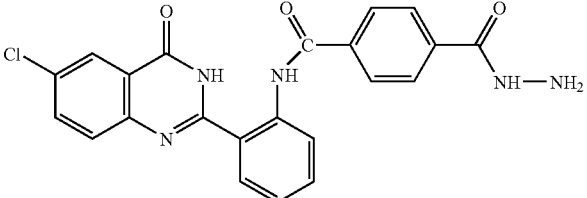Compound 21 | 4 | yellow/green |
| 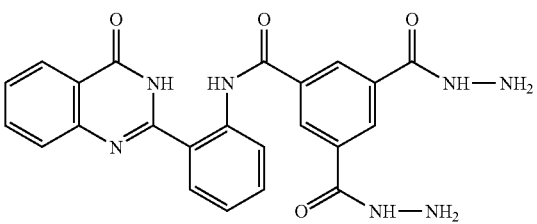Compound 22 | 4 | green |
| 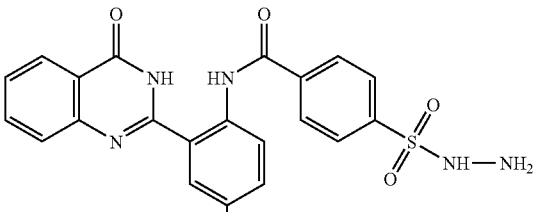Compound 23 | 4 | yellow |
| 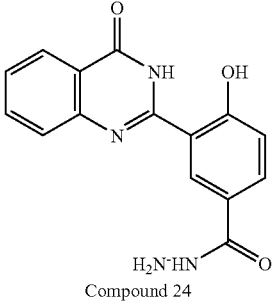Compound 24 | 4 | yellow/green |
| 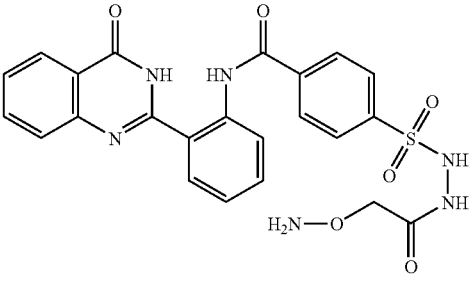Compound 25 | 4 | yellow/green |

TABLE 2-continued
| Compound | Prepared as in Example: | Fluorescence color |
|---|---|---|
| 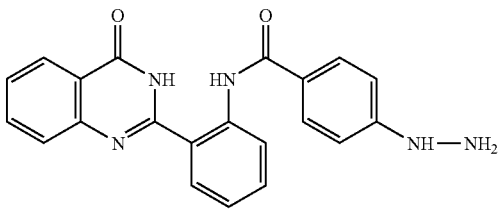  Compound 26 | 12 | green/blue |
| 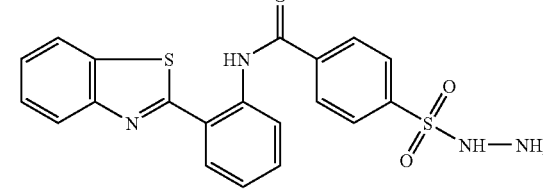  Compound 27 | 4 | green |
| 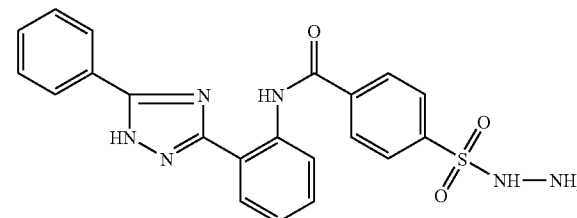  Compound 28 | 4 | blue |
| 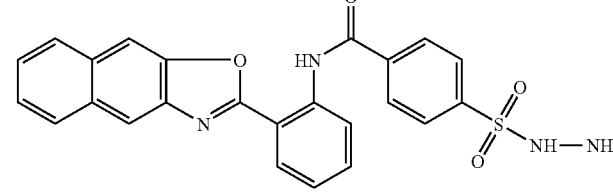  Compound 29 | 4 | yellow/green |
| 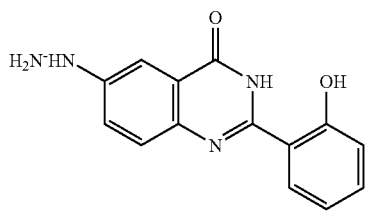  Compound 30 | 12 | green/blue |
| 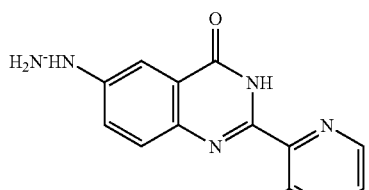  Compound 31 | 12 | blue |

TABLE 2-continued

| Compound | Prepared as in Example: | Fluorescence color |
|---|---|---|
| 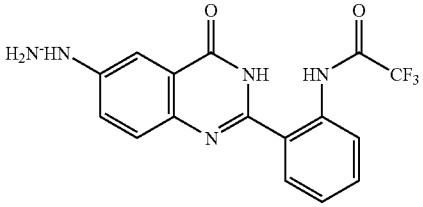
Compound 32 | 12 | green |
| 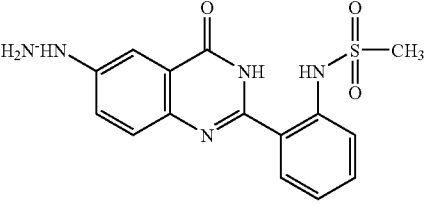
Compound 33 | 12 | yellow |
| 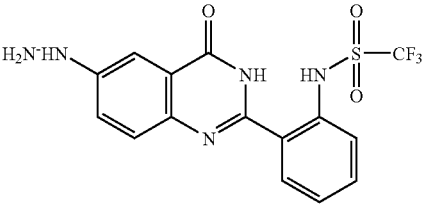
Compound 34 | 12 | yellow/orange |
| 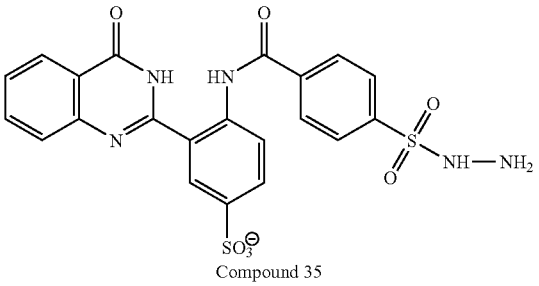
Compound 35 | 4 | yellow/green |

EXAMPLE 19

Detection of Glycoproteins in SDS Polyacrylamide Gels

Proteins of interest were separated by SDS-polyacrylamide gel electrophoresis utilizing a 4% T, 2.6% C stacking gel, pH 6.8 and 15% T, 2.6% C separating gel, pH 8.8, according to standard procedures. % T is the total monomer concentration (acrylamide+crosslinker) expressed in grams per 100 mL and % C is the percentage crosslinker (e.g. N,N'-methylene-bis-acrylamide, N,N'-diacryloylpiperazine or other suitable agent). After electrophoresis, gels were incubated in 50% methanol for 30 minutes, in two changes of 3% acetic acid for 5 minutes, and then in 1% periodic acid prepared in 3% acetic acid for 30 minutes. Alternative oxidizing agents might include chromic acid, permanganate, lead tetraacetate, sodium bismuthate, manganese acetate or phenyl iodoacetate. Gels were then washed in 3% acetic acid for 4×10 minutes, and incubated for 30-120 minutes in a solution of 5 µM Compound 5, 3% acetic acid, 2% dimethylformamide, and 0.25 M magnesium chloride. The salt may be omitted, but staining intensity is decreased. Other salts may be used instead of magnesium chloride, including sodium chloride and magnesium sulfate. After labeling with the reagent, gels were rinsed in 3% acetic acid twice for 5 minutes each. Glycoproteins may be viewed using a 300 nm UV transilluminator. Proteins appeared as green luminescent bands on a clear background (Fluorescence excitation/emission spectra for Compound 5-labeled α1-acid glycoprotein are given in FIG. 1).

EXAMPLE 20

Detection of Glycoproteins in Isoelectric Focusing Gels

Isoelectric focusing (IEF) can be performed utilizing a variety of pre-cast and laboratory prepared gels that employ different chemistries to generate a pH gradient. In this instance, Ampholine PAG plates were run horizontally for 1500 volt-hours using a Multiphor II electrophoresis unit (Amersham-Pharmacia Biotech, Uppsala, Sweden) per the manufacturer's instructions. In another alternative, denaturing, 1 mm IEF slab gels were cast utilizing a 4% T, 2.6% C polyacrylamide gel matrix, containing 9 M urea, 2% Triton X-100, and 2% carrier ampholytes. Electrophoresis was performed on a Multiphor II electrophoresis unit for 1500 volt-hours using 10 mM phosphoric acid and 100 mM sodium hydroxide as anode and cathode buffer, respectively. Luminescent staining of glycoproteins in gels was performed by immersing the gel in 50% methanol for 30 minutes, in two changes of 3% acetic acid for 5 minutes, and then in 1% periodic acid in 3% acetic acid for 30 minutes. Gels were then washed in 3% acetic acid for 4×10 minutes, then incubated for 30-120 minutes in a solution of 5 µM Compound 23, 3% acetic acid, 2% dimethylformamide, and 0.25 M magnesium chloride. Gels were then rinsed in two changes of water for one hour each and viewed by illumination with a 300 nm UV light source. Glycoproteins appeared as green luminescent bands on a clear background.

EXAMPLE 21

Detection of Glycoproteins in Two-Dimensional Gels

A mouse 3T3 fibroblast cell lysate protein mixture was solubilized in 8 M urea, 2% Triton X-100, 2% carrier ampholytes, 100 mM dithiothreitol, 0.1% sodium dodecyl sulfate, 12.5 mM Tris, pH 8.0. Approximately 50 µg of protein was applied to 1 mm diameter, 20 cm long isoelectric focusing gels consisting of a 4% T, 2.6% C polyacrylamide gel matrix, containing 9 M urea, 2% Triton X-100, and 2% carrier ampholytes. Gels were run vertically for 18,000 volt-hours using 10 mM phosphoric acid and 100 mM sodium hydroxide as anode and cathode buffer, respectively. Isoelectric focusing gels were incubated in 0.3 M Tris base, 0.075 M Tris-HCl, 3% SDS, 0.01% bromophenol blue for two minutes. Isoelectric focusing gels were then laid on top of 1 mm thick, 20 cm×20 cm, 12.5% T, 2.6% C polyacrylamide gels containing 375 mM Tris-base, pH 8.8 and SDS-polyacrylamide gel electrophoresis was performed according to standard procedures except that the cathode electrode buffer was 50 mM Tris, 384 mM glycine, 4% sodium dodecyl sulfate, pH 8.8 while the anode electrode buffer was 25 mM Tris, 192 mM glycine, 2% sodium dodecyl sulfate, pH 8.8. After the second dimension electrophoresis, gels were incubated in 50% methanol for 30 minutes, in two changes of 3% acetic acid for 5 minutes, and then in 1% periodic acid in 3% acetic acid for 30 minutes. Gels were then washed in 3% acetic acid for 4×10 minutes, then incubated for 30-120 minutes in a solution of 5 µM Compound 5, 3% acetic acid, 2% dimethylformamide, and 0.25 M magnesium chloride. Gels were rinsed in dd $H_2O$ for 10-15 minutes and viewed using a 300 nm UV transilluminator. Glycoproteins appeared as green luminescent spots on a clear background. The majority of glycoproteins were observed to have an isoelectric point that was less than 5.5 in this sample.

EXAMPLE 22

Serial Dichromatic Detection of Glycosylated and Nonglycosylated Proteins in Two-Dimensional Gels Two-dimensional gel electrophoresis was performed as described in Example 21. Glycoprotein detection was performed in the same manner as well. The signal from the green fluorescent glycoproteins was collected with a standard CCD camera-based imaging system using a 520 nm bandpass filter. After detection of the glycoproteins, the gel was stained with SYPRO RUBY protein gel stain (Molecular Probes, Eugene, Oreg.) by incubating the gel for 3-20 hours in the stain, and then incubating the gel in 7% acetic acid, 10% methanol for 30 minutes. The orange signal from the glycosylated and nonglycosylated proteins was collected with a standard CCD camera-based imaging system with a 600 nm bandpass filter or a 610 nm longpass filter.

EXAMPLE 22a

Dichromatic Detection of Glycosylated and Nonglycosylated Proteins in Two-Dimensional Gels Alternatively, the two-dimensional gels may be stained with SYPRO RUBY protein gel stain first, followed by detection of glycoproteins using Compound 5. Both reagents were excited by 300 nm UV illumination but their emission maxima differ by 80 nm. Upon illumination using a standard UV transilluminator glycoproteins appeared green while nonglycosylated proteins appeared orange. Using a standard CCD camera-based imaging system, the two signals may be imaged separately using a 520 nm band pass filter to collect signal from the Compound 5 and a 640 nm band pass filter to collect the signal from SYPRO RUBY protein gel stain.

EXAMPLE 23

Detection of Glycoproteins Electroblotted to PVDF or Nitrocellulose Membranes

Proteins of interest were separated by SDS-polyacrylamide gel electrophoresis and transferred to PVDF or nitrocellulose membrane using standard procedures. Following dot- or slot-blotting, membranes were allowed to air dry to minimize loss of protein during subsequent staining steps. The membrane was subsequently immersed in 50% methanol (for PVDF membrane) or 10% methanol (for nitrocellulose membrane) for 30 minutes, in two changes of 3% acetic acid for 5 minutes, and then in 1% periodic acid in 3% acetic acid for 30 minutes. The blots were then washed in three or four changes of 3% acetic acid for 5-10 minutes. Blots were then incubated for 30-120 minutes in a solution of 5 µM Compound 5, 3% acetic acid, 2% dimethylformamide, and 0.25 M magnesium chloride. The membrane was incubated for 5 minutes each in four changes of dd-$H_2O$. The membrane was allowed to air dry and was subsequently viewed using a reflective or transmissive 300 nm UV light source. Glycoproteins appeared as bright green luminescent bands on a faint blue or green background. The signal from the green fluorescent glycoproteins was collected with a standard CCD camera-based imaging system using a 520 nm bandpass filter. Serial dichromatic detection of glycosylated and nonglycosylated proteins on PVDF membranes was accomplished by floating the membrane face down on a solution of 10% methanol, 7% acetic acid for 10 minutes followed by face staining with SYPRO RUBY blot stain for 15 minutes. The membrane was washed face down on water, 3 changes in 5 minutes. The membrane was allowed to air dry. The fluorescent signal from total proteins was detected using a standard CCD camera-based imaging system with a 520 nm longpass filter. Alternatively dichromatic detection of nonglycosylated proteins and glycoproteins was accomplished with the orange fluorescent signal due to SYPRO Ruby stain collected using a 640 nm longpass filter, and the green signal due to glycoproteins stained with Compound 5 was collected using a 520 nm bandpass filter. Alternatively, a PVDF membrane containing electroblotted proteins was stained with SYPRO RUBY protein blot stain followed by staining with Compound 5, as above, and serial dichromatic staining accomplished as above.

EXAMPLE 24

Mobility-Shift Gel Analysis Using Deglycosylating Enzymes and Detection with either SYPRO RUBY Protein Gel Stain for Visualization of Total Proteins or a Reagent of the Invention for Detection of Glycosylated Proteins In the assay, glycoproteins were incubated with glycosidase enzymes and compared with undigested proteins using SDS-polyacrylamide gel electrophoresis. Deglycosylation was performed by standard methods using commercially available kits such as the Prozyme Glycopro Deglycosylation kit (Prozyme Inc, San Leandro, Calif.). Typically, these kits contain PNGase F to remove N-linked glycans, Endo-O-Glycosidase to remove O-linked glycans and Sialidase A to remove sialic acid residues. Control, undigested proteins were loaded into lanes of a standard 13% SDS-polyacrylamide gel as well as the corresponding proteins after incubation with glucosidases. Suitable test proteins include α1-acid glycoprotein, horseradish peroxidase, bovine fetuin; ovalbumin and PHA-M lectin. SDS-polyacrylamide gel electrophoresis was performed by standard procedures. Serial dichromatic staining was performed as described in Example 22. The signal from the green fluorescent gylcoproteins was collected with a standard CCD camera-based imaging system using a 520 nm bandpass filter. After detection of the glycoproteins, the gel was stained with SYPRO RUBY protein gel stain (Molecular Probes, Eugene, Oreg.) by incubating the gel for 3-20 hours in the stain, and then incubating the gel in 7% acetic acid, 10% methanol for 30 minutes. The orange signal from the glycosylated and nonglycosylated proteins was collected with a standard CCD camera-based imaging system with a 600 nm bandpass filter or a 610 nm longpass filter. Without exposure to glycosidases, the glycoproteins α1-acid glycoprotein, horseradish peroxidase, fetuin, ovalbumin and PHA-M lectin were detected with both stains. After glycosidase treatment, α1-acid glycoprotin, fetuin, ovalbumin and PHA-M showed a marked mobility shift as detected by SYPRO RUBY protein gel staining and loss of staining by the reagent of the invention, indicating that the carbohydrate groups were cleaved off. However, the horseradish peroxidase did not show a substantial mobility shift, although staining with Compound 5 shows that it contained a significant amount of carbohydrate. This protein contained an α-(1,3)-fucosylated asparagine N-acetylglucosamine-linkage that was resistant to cleavage by the glycosidases used in this study. Thus, the use of the Compound 5 identified glycoproteins not susceptible to glycosidases used in the mobility-shift assay, providing important information about the glycoprotein's carbohydrate structure.

EXAMPLE 25

Detection of Glycoprotein in Filtration Plates

Prior to protein application the hydrophobic membranes in individual wells of a 96-well Millipore MultiScreen filtration plate are wetted with methanol and then rinsed with 7% acetic acid using a vacuum manifold per manufacturer's instructions (Millipore Corporation, Bedford, Mass.). 0.2 to 1000 ng/mm$^2$ of ovalbumin is applied to individual wells without application of a vacuum. The plate is incubated for 30-60 minutes before protein is removed by application of a vacuum. The filtration plate is then allowed to air dry and wells are incubated in 50% methanol for 30 minutes, in two changes of 3% acetic acid for 5 minutes, and then in 1% periodic acid in 3% acetic acid for 30 minutes. Wells are then rinsed in 3% acetic acid and incubated for 30 minutes in a solution of 5 µM Compound 5, 3% acetic acid, 2% dimethylformamide, and 0.25 M magnesium chloride. The dye solution is removed from the wells by pipetting and 200 µL of 3% acetic acid is applied and removed by pipetting 3-4 times to remove any unbound dye. The filtration plate is subsequently read using a Perkin-Elmer HTS 7000 microplate reader or similar device. An excitation filter of 300 nm and an emission filter of 530 nm is selected. Measurements are made through the top face of the plate. Instrument software provides digital values corresponding to the luminescence intensity of the signal from the dye in each well.

EXAMPLE 26

Detection of Lipopolysaccharides in SDS Polyacrylamide Gels

A serial dilution of *Escherichia coli* serotype 055:B5 lipopolysaccharide ranging from 1 to 4000 nanograms was separated by SDS gel electrophoresis using a 15% T, 2.6% C polyacrylamide gel. The gel was subsequently immersed in 50% methanol for 30 minutes, in two changes of 3% acetic acid for 5 minutes, and then in 1% periodic acid in 3% acetic acid for 30 minutes. Gels were rinsed 4×5 minutes in 3% acetic acid, then incubated for 30 minutes in a solution of 5 µM Compound 5, 3% acetic acid, 2% dimethylformamide, and 0.25 M magnesium chloride. Afterwards, the gel was rinsed in 3% acetic acid for 5 minutes and placed on a 300 nm UV transilluminator. The separated lipopolysaccharides appeared as bright green luminescent bands with little or no background signal. The capability of Compound 5 to detect bacterial lipopolysaccharides was compared with that of an alkaline silver diamine-based stain (Silver Stain Plus, Bio-Rad Laboratories, Hercules, Calif.). The alkaline silver diamine stain was selected because it is superior to an acidic silver nitrate stain, zinc-imidazole stain, SYPRO ORANGE stain and SYPRO RUBY protein gel stain in terms of its ability to detect lipopolysaccharides. Detection of as little as 2-8 ng of total applied lipopolysaccharide after SDS-polyacrylamide gel electrophoresis was possible using Compound 5 while only 250-1000 ng can be detected using the silver staining method. Using Compound 5, the linear dynamic range for detection of lipopolysaccharide extended from 2-4000 ng of applied material ($r^2$=0.9901). Similar results were obtained when lipopolysaccharides from *Pseudomonas aeruginosa*, serotype 10 or *Escherichia coli* EH100 (RA mutant) are evaluated. It should be noted that the lipolysaccharides typically separate into roughly 20 bands, and that the detection sensitivity of the individual components was substantially below a single nanogram using Compound 5. Lipooligosaccharides, the major glycolipids expressed on mucosal Gram-negative bacteria may be detected by similar procedures, and may provide a means to distinguish Gram positive and Gram negative bacteria.

EXAMPLE 27

Detection of Glycogen Slot-Blotted onto PVDF Membranes

A serial dilution of glycogen was prepared in deionized water or other suitable solution such as 7% acetic acid or 20 mM Tris HCl, pH 6.8, 500 mM NaCl. For dot-blotting, 1-5 µL volumes of the glycopolymer are applied to a 0.4 µm pore size wetted PVDF membrane using a pipetter. Slot-blotting was performed using a Bio-Dot SF vacuum apparatus (Bio-Rad Laboratories, Hercules, Calif.). For slot-blotting, membranes were rehydrated with methanol, then 100 µl/well dd-$H_2O$, samples were applied to the membranes (200 µl/well), wells were rinsed twice with 600 µL of 7% acetic acid/10% methanol and twice with 600 µL of dd-$H_2O$. Following dot- or slot-blotting, membranes were allowed to air dry to minimize loss of polymer during subsequent staining steps. The membrane was subsequently immersed in 50% methanol for 30 minutes, in two changes of 3% acetic acid for 5 minutes, and then in 1% periodic acid in 3% acetic acid for 30 minutes. Blots were rinsed 4×5 minutes in 3% acetic acid, and then incubated for 30-120 minutes in a solution of 5 µM Compound 5, 3% acetic acid, 2% dimethylformamide, and 0.25 M magnesium chloride. The membrane was incubated for 5 minutes each in four changes of dd-$H_2O$. The membrane was allowed to air dry and was subsequently viewed using a reflective or transmissive 300 nm UV light source. Spotted glycogen appeared as green luminescent bands on a faint fluoroescent blue background. The limits of detection is typically 4-8 ng of glycogen and the linear dynamic range of detection extends from 16 to 250 ng of applied material ($r^2$=0.958). Other glycopolymers such as starch, chitin, cellulose and pectin should be detectable using similar methods. Parallel experiments performed with chondroitin-4-sulfate reveal that the detection sensitivity for this glycosaminoglycan is quite poor, with limits of detection in the vicinity of 16 µg of applied material. This is not unexpected as glycosaminoglycans such as chondroitin sulfate, hyaluronic acid, dermatan sulfate, alginates, fucoidan, carrageenans and keratan sulfate are known to stain poorly by conventional periodic acid Schiff's procedures.

EXAMPLE 28

Pre-Derivatization of Glycoproteins Followed by SDS-Polyacrylamide Gel Electrophoresis A glycoprotein such as horseradish peroxidase is diluted to 5 mg/mL in 100 mM sodium acetate buffer, pH 5.0 containing 10 mM in sodium periodate and then the sample is incubated in the dark for 2 hours. The sample is then diluted 2 fold into a solution of 10 µM Compound 5, 6% acetic acid, 4% dimethylformamide, and 0.5 M magnesium chloride and incubated for 30 minutes to 2 hours. Afterwards, the protein sample is added to a sufficient amount of ice-cold acetone to yield an 80% acetone solution. After incubating on ice for 10 minutes, the sample is centrifuged at 14,000×G using a tabletop microcentrifuge, the supernate is discarded and the pellet is resuspended in standard SDS sample buffer. The sample is heated to 100° C., cooled to room temperature and then applied to a 13% T, 2.6% C SDS-polyacrylamide gel. Electrophoresis is performed by standard methods and the gel is then placed upon a 300 nm UV transilluminator. The glycoprotein appears as a green fluorescent band in the gel.

EXAMPLE 29

Specific Detection of DNA after Polyacrylamide Gel Electrophoresis

Figure 7:
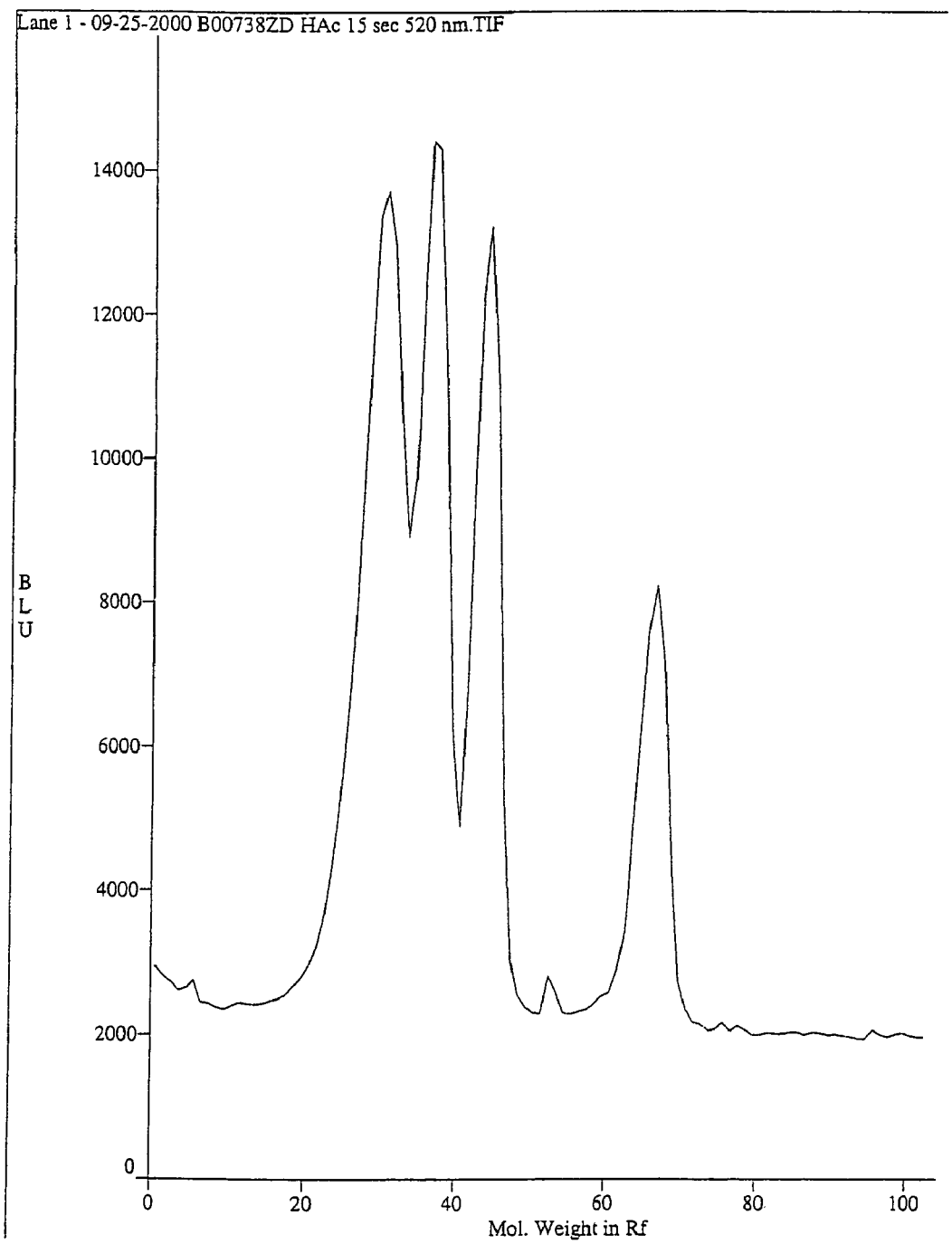
FIG. 7: Intensity profile of electrophoretically separated DNA molecular weight standards using Compound 5 (as described in Example 29). Lanes loaded with ribosomal RNA failed to label with Compound 5. Less than 1 ng of acid-treated DNA could be detected, thus providing detection sensitivity comparable to ethidium bromide. Unlike ethidium bromide, this procedure fails to detect even 500 ng of rRNA.

Two-fold serial dilutions of Hae III-cleaved φX174 RF DNA starting with 200 ng as well as 2-fold serial dilutions of ribosomal RNA starting at 500 ng were prepared in native loading buffer (5% glycerol), heat-denatured at 95° C., quick-cooled on ice, loaded onto 0.75 mm thick 5% T, 5% C polyacrylamide gels and separated by electrophoresis for 3-4 hours in 89 mM Tris borate, 2 mM EDTA, pH 8.3 (TBE buffer) at 60 volts by standard procedures. After electrophoresis, gels were incubated for 30 minutes in 50% methanol, and then incubated in 5 M HCl at room temperature for 20 minutes. Gels were incubated in 3% acetic acid for 5 minutes and then incubated in 5 µM Compound 23, 3% acetic acid, 2% dimethylformamide, and 0.25 M magnesium chloride for 30-120 minutes. Gels were then rinsed in 3% acetic acid and placed onto a 300 nm UV transilluminator. 1 ng of DNA was readily detected by this method as fluorescent green bands. In comparison, ribosomal RNA (500 ng) was not labeled by this method. The cited labeling procedure was based upon the histological Feulgen reaction, where hydrolysis by HCl frees the aldehyde groups of deoxyribose, and may also be used to selectively detect DNA in cells. An intensity profile of electrophoretically separated DNA molecular weight standards using Compound 5 is given in FIG. 7.

EXAMPLE 30

Detection of both DNA and RNA after Polyacrylamide Gel Electrophoresis

Dilution series of DNA and RNA are prepared and subjected to electrophoresis as described in Example 29. Gels are then incubated in 100 mM sodium acetate buffer, pH 4.5 containing 1 M sodium bisulfite, 10 µM Compound 5. The gels are incubated at 37° C. for 24 hours. Cytosine residues are converted to 6-sulfo-cytosine residues and Compound 5 is then incorporated by a transamination reaction. Gels are incubated in 3% acetic acid for 5 minutes and then placed on a 300 nm UV transilluminator. Both DNA and RNA appear as fluorescent green bands on a pale blue fluorescent background.

EXAMPLE 31

Immunodetection of Tubulin using Oxidized HRP-Conjugated Secondary Antibody Approximately 1-2000 ng of bovine brain tubulin prepared in a constant amount of broad range molecular weight standards (300 ng/protein band) was applied per gel lane and separated by SDS-polyacrylamide gel electrophoresis utilizing a 4.25% T, 2.6% C stacking gel, pH 6.8 and 13% T, 2.6% C separating gel, pH 8.8 by standard methods. Gels were transferred to PVDF membranes by standard methods. Blots were subsequently incubated three times for 10 minutes each in modified Tris-buffered saline equilibration buffer (MTBS; 50 mM Tris base, 150 mM NaCl, pH 7.5) and then for 60 minutes in MTBS containing 0.2% Tween-20 and 0.5% poly (vinylalcohol) (PVA; 30,000-70,000 Da, Sigma Chemical). Monoclonal anti-tubulin antibody (Molecular Probes, Eugene, Oreg.) was diluted 1:500 in MTBS/Tween-20/PVA and blots were incubated in the solution overnight. Blots were then rinsed in MTBS/Tween-20/PVA 4 times for 10 minutes each. Blots were then incubated for 60 minutes in 1:10,000 dilution of oxidized horseradish peroxidase-conjugated secondary antibody prepared in MTBS/Tween-20/PVA. Oxidation of the conjugate was accomplished by incubating 5 mg/mL of the protein conjugate in 100 mM sodium acetate buffer, pH 4.5 containing 10 mM sodium periodate for 2 hours in the dark. The reaction was terminated by the dilution step prior to application to the membrane. After incubating in the secondary antibody, blots were incubated in four changes of MTBS/Tween-20/PVA for 5 minutes each and then in 5 µM Compound 5, 3% acetic acid, 2% dimethylformamide, and 0.25 M magnesium chloride. The membrane was rinsed in 3% acetic acid for 10 minutes and fluorescent signal was visualized using a Lumi-Imager CCD-based computerized image analysis system (Roche Biochemicals, Indianapolis, Ind.). Tubulin appeared as a white band against a black background on the computer monitor.

EXAMPLE 32

Converting Compound 5 into a Red-Emitting Stain

An SDS-polyacrylamide gel containing a mixture of glycosylated and unglycosylated protein molecular weight standards was treated with Compound 5 as described in Example 19. The gel was incubated in 3% acetic acid for 10 minutes and then incubated in a 1:5000 dilution of SYPRO RED protein gel stain (Molecular Probes, Eugene, Oreg.) prepared in 3% acetic acid, 0.001% SDS. The gel was incubated in the staining solution for 90 minutes and then briefly rinsed in 3% acetic acid. Using a UV transilluminator, glycoproteins appeared as bright red bands with nonglycosylated proteins more faintly stained. Using a 520 nm band pass filter revealed that the green signal from Compound 5 had diminished substantially. Analysis of the gel on a laser gel scanner, such as the Fuji FLA-3000 (Fuji Film Co., Tokyo, Japan), using the 532 nm second harmonic generation laser revealed that the proteins were fairly uniformly labeled with SYPRO RED dye. Without wishing to be bound by theory, this example illustrates that Compound 5 absorbs UV radiation and transfers it to SYPRO RED dye where it is emitted at a substantially longer wavelength (640 nm). This increases the effective Stoke's shift of the glycoprotein detection system from 245 to 350 nm.

EXAMPLE 33

Edman Sequencing of Glycoproteins Electroblotted to Transfer Membranes

Glycoproteins of interest are subjected to electrophoresis, subsequently transferred to poly (vinylidene difluoride) membrane and stained as described in Example 27. After target proteins are identified, the bands are excised with a sharp razor. For internal protein sequencing, the target proteins are excised from the membrane, subjected to in-situ proteolytic cleavage, for 3 hours at 37° C., and in the presence of 10% acetonitrile, 3% Tween-80 in 100 mM $NH_4HCO_3$, pH 8.3. Resulting fragments are then separated by micro-bore reverse phase HPLC. Selected peak fractions are analyzed by automated Edman degradation. Glycoproteins subjected to Edman sequencing are expected to produce high quality spectra with excellent initial and repetitive sequencing yields.

EXAMPLE 34

Matrix-Assisted Laser Desorption Mass Spectrometry-Based Identification of Glycoproteins Electroblotted to Transfer Membranes Glycoproteins of interest were subjected to electrophoresis, subsequently transferred to poly (vinylidene difluoride) membrane and stained as described in Example 27. After target proteins were identified, the bands were excised with a sharp razor. Bands were then washed 3 times 5 minutes in 25 mM ammonium bicarbonate pH 7.8, 10% methanol and allowed to dry. After drying, the bands were cut into 1-2 mm squares and incubated in 20 µg/mL trypsin in digestion buffer (25 mM ammonium bicarbonate, pH 7.8 with 1% octyl β-glucoside and 10% methanol added). Sufficient volume of the trypsin digestion mixture was added to cover the membrane squares. Proteins were digested at room temperature for 5-6 h and then incubated overnight at 27-28° C. The peptides were extracted with formic acid:ethanol (1:1), and then lyophilized. After lyophilization, the peptides were resuspended in water for analysis by matrix assisted laser desorption ionization mass spectrometry (MALDI-MS). Equal volumes of the peptide digests were mixed with α-cyano-4-hydroxycinnamic acid matrix (10 mg/mL in 70% acetonitrile/$H_2O$). The mixture was spotted onto the sample plate and air dried prior to analysis. MALDI-MS analysis was performed in a Voyager Mass Spectrometer, (PerSeptive BioSystems, Framingham, Mass., USA). The instrument was calibrated with Substance-P (1347.7 Da) and insulin (5731.4 Da). The peptide masses obtained from the trypsinized protein were used to search the EMBL peptide database using the PeptideSearch engine available on the world wide web, (www.mann.embl-heidelberg.de). Proteins were expected to be readily identified with good peptide sequence coverage.

EXAMPLE 35

Oligosaccharide Profiling

A glycoprotein, such as α1 acid-glycoprotein (50-500 µg), is prepared in 5 µL of 1% SDS, 0.5 M 2-mercaptoethanol, 0.1 M EDTA and incubated at room temperature for 30 minutes. The sample is then diluted with 40 µL of 0.2 mM sodium phosphate buffer, pH 8.6 and mixed thoroughly. The sample is heated in a boiling water bath for 5 minutes and then allowed to cool to room temperature. 5 µL of 7.5% Nonidet P-40 is added, the sample is mixed and 5 µL PNGase F (1.0 unit) is added. The tube is mixed thoroughly and then incubated at 37° C. for 20 hours. Then, 165 µL cold ethanol is added and the sample is incubated on ice for at least 1 hour. The sample is centrifuged at 10,000 g for 2 minutes at room temperature. The supernate, containing the released glycans is collected and dried using a centrifugal vacuum evaporator. The dried glycans are suspended in 20 µL 5 µM Compound 35, 3% acetic acid, 2% dimethylsulfoxide and incubated for 16 hours at 37° C. Sodium cyanoborohydride may optionally be added to this reaction mixture. Dry the sample mixture in a centrifugal vacuum evaporator for about 1 hour. Though some heating may be required to vaporize the DMSO, temperatures greater than 45° C. should be avoided. The dried sample is dissolved in glycerol-water (1:4, v/v). The derivatized oligosaccharides are separated on a 14 cm long 30% T, 2.6% C polyacrylamide gel and electrophoresis is performed using standard protocols, omitting SDS from the gels and buffers. Sulfonated versions of the reagents of the invention are preferred for this application as they confer a negative charge to neutral and weakly charged glycans. Tris-borate gel buffer systems allow unsulfonated reagents to be used for the detection of neutral glycans, however, as commonly used with 2-aminoacridone-derivatized glycans. After electrophoresis, green fluorescent bands may be visualized by eye, by photography or by CCD-camera-based imaging.

EXAMPLE 36

Cytochemical Detection of DNA in Cells

MRC-5 human lung fibroblasts, NIH-3T3 murine fibroblasts, and bovine pulmonary artery endothelial cells were removed from culture and washed twice with warm phosphate-buffered saline (PBS) at pH 7.4. Cells were then fixed with cold 100% ethanol at −20° C. for 10 minutes, washed twice with PBS, and incubated in 5 N hydrochloric acid for 30 minutes at 25° C. The samples were then washed twice in PBS and incubated in 5 μM Compound 5, 3% acetic acid, 2% dimethylformamide, 0.25 M magnesium chloride for 120 minutes at 25° C., protected from light. Samples were washed twice in 3% acetic acid and mounted in a glycerol-based mounting medium before being sealed with paraffin wax for observation. Fluorescence microscopy was performed using a Nikon Eclipse 800 upright microscope equipped with a 100 watt mercury light source. Visualization of the fluorescent signal was accomplished using filters with an excitation wavelength between 320-400 nm and an emission filter with wavelengths between 500-560 nm. Images were acquired using a MicroMax 1300 YHS, 12 bit digital camera (Princeton Instruments, Inc.), controlled using MetaMorph software (Universal Imaging Corp). Microscopic observation revealed distinct nuclear green fluorescent signal in acid-treated cells and no signal in untreated samples. At high magnification, punctate cytoplasmic signal was observed which may represent mitochondrial DNA.

EXAMPLE 37

Cytochemical Detection of Polysaccharides in Plastic-Embedded Tissue

Aldehyde blockage is performed using chlorous acid as described in Example 36. Alternatively, thiosemicarbazide blockage (1 mg/mL methylcellosolve: acetic acid, 95:5) may be employed instead. In this case the sample is incubated for 30 minutes at 25° C. in the blocking solution. The sample is then rinsed in distilled water for 10 minutes, then treated with 1% periodic acid in water for 10 minutes. The sample is washed in distilled water for 5 minutes and then stained in 5 μM Compound 5, 3% acetic acid, 2% dimethylformamide, and 0.25 M magnesium chloride for 15-20 minutes. The sample is then rinsed in distilled water for 5 minutes, blow-dried and mounted using standard methods. Polysaccharides such as glycogen are observed to be bright green by fluorescence microscopy.

EXAMPLE 38

Preparation of a Reagent-Dextran Conjugate

A solution of carboxymethyldextran (average MW 70,000) having approximately 20 carboxylic acid groups is prepared by dissolved the dextran in water whose pH has been adjusted to 6.0 to a final concentration of 10 mg/mL. The solution resulting is treated with 5 equivalents of ethyldimethylaminopropylcarbodiimide (EDAC) for 15 minutes at room temperature with stirring. To the solution is then added 1 equivalent of Compound 5, and the reaction mixture is stirred overnight. The solution is then poured into ethanol, and the resulting precipitate is separated from unconjugated Compound 5 by extensive dialysis against pH 7 phosphate buffer, then water. The solution of conjugated dextran is lyophilized to yield a green-fluorescent solid that should be useful as a fluorescent tracer.

It is to be understood that, while the foregoing invention has been described in detail by way of illustration and example, numerous modifications, substitutions, and alterations are possible without departing from the spirit and scope of the invention as described in the following claims.

What is claimed is:

1. A kit, the kit comprising:
   a) a ketone- or aldehyde-reactive compound having the formula:

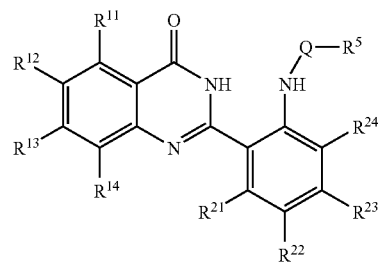

wherein Q is carbonyl, thiocarbonyl, or sulfonyl, and $R^5$ is -L-Z;

L is arylene, or a $C_{1-6}$ perfluoroalkylene; and

Z is a $(C=O)NR^6NH_2$, $-NR^6-NH_2$, $-(SO_2)NR^6NH_2$ or $-(C=S)NR^6NH_2$,
   wherein $R^6$ is hydrogen or $C_{1-6}$ alkyl;

$R^{11}$, $R^{12}$, $R^{13}$ and $R^{14}$ are independently H, $C_{1-6}$ alkyl, $C_{1-6}$ alkylamino, amino, or halogen; and $R^{21}$, $R^{22}$, $R^{23}$, and $R^{24}$ are independently H, $C_{1-6}$ alkyl, $C_{1-6}$ alkoxyl, $C_{1-6}$ perfluoroalkyl, $C_{1-6}$ alkylamino, di($C_{2-12}$-alkyl)amino, amino, carboxy, cyano, halogen, hydroxy, nitro, phenyl, sulfo, or -L-Z; and b) instructions for labeling an aldehyde- and/or ketone-containing target substance, wherein said compound is present as a stock solution in an organic solvent.

2. The kit according to Claim 1, further comprising an oxidizing agent where the oxidizing agent is periodate.

3. The kit according to claim 1, further comprising a nucleic acid stain as an additional detection reagent where the nucleic acid stain is selected from the group consisting of thiazole orange, ethidium homodimer, ethidium bromide, and propidium iodide.

4. The kit according to claim 1, wherein the compound is:

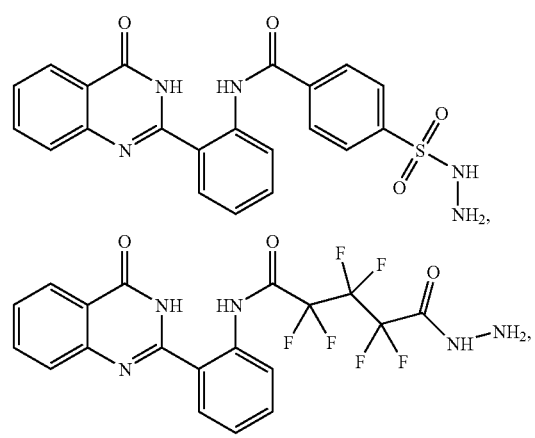

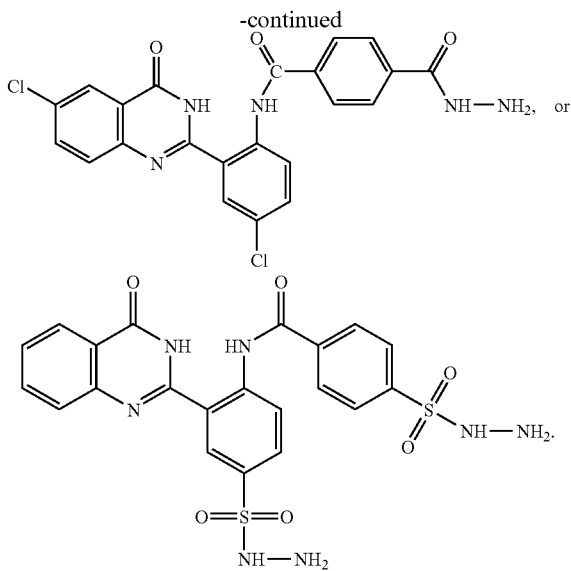

5. The kit according to claim 1, further comprising a buffering agent selected from the group consisting of N,N-bis[2-hydroxyethyl]-2-aminoethanesulfonic acid, 2-[bis(2-hydroxyethyl)amino]ethanesulfonic acid), N,N-bis[2-hydroxyethyl]glycine, 3-[cyclohexylamino]-1-propanesulfonic acid, N-[2-hydroxyethyl]piperazine-N'-[3-propanesulfonic acid], N-[2-hydroxyethyl]piperazine-N'-[2-ethanesulfonic acid], 2-[N-morpholino]ethanesulfonic acid, 3-[N-morpholino]propanesulfonic acid, piperazine-N,N'-bis [2-ethanesulfonic acid], 1,4-piperazinediethanesulfonic acid), N-tris [hydroxymethyl]methyl-3-aminopropanesulfonic acid, [2-hydroxy-1, 1-bis(hydroxymethyl)ethyl] amino-1-propanesulfonic acid, (N-tris[hydroxymethyl]methyl-2-aminoethanesulfonic acid, 2-([2-hydroxy-1,1-bis(hydroxymethyl)ethyl]amino)ethanesulfonic acid), (N-tris [hydroxymethyl]methylglycine, and N-[2-hydroxy-1,1-bis (hydroxymethyl)ethyl] glycine.

6. The kit according to claim 1, further comprising a buffering agent selected from the group consisting of salts of formate, citrate, acetate, N-(2-hydroxyethyl)-N'-(2-sulfoethyl)piperazine, imidazole, N-(2-hydroxyethylpiperazine)-N'-2-ethanesulfonic acid, Tris(hydroxymethyl)aminomethane acetate, and Tris (hydroxymethyl)aminomethane hydrochloride.

7. The kit according to claim 1, further comprising a buffering agent selected from the group consisting of 2-[N-morpholino]ethanesulfonic acid, sodium acetate, and acetic acid.

8. The kit according to claim 7, wherein the buffering agent is acetic acid.

9. The kit according to claim 1, further comprising an inorganic salt selected from the group consisting of sodium chloride, ammonium sulfate, magnesium chloride, magnesium acetate, zinc chloride, magnesium sulfate and magnesium glucuronate.

10. The kit according to claim 9, wherein the inorganic salt is sodium chloride or magnesium chloride.

11. The kit according to claim 10, wherein the inorganic salt is magnesium chloride.

12. The kit according to claim 1, wherein the organic solvent is selected from the group consisting of dimethylsulfoxide, dimethylformamide, methanol, and ethanol.

13. The kit according to claim 1, wherein the stock solution is at a concentration of greater than about 50-times that used in a final staining solution.

14. The kit according to claim 1, wherein the target substance is selected from the group consisting of formaldehyde, acetone, benzaldehydes, reducing sugars and polysaccharides in ring-opened forms, steroids, keto acids, aldehyde- or ketone-containing drugs, aldehyde- or ketone-containing environmental pollutants, aldehyde- or ketone-containing organics, acid-treated deoxyribonucleic acids, oxidized sugars, oxidized polysaccharides, oxidized glycols, oxidized glycoproteins, oxidized glycolipids, oxidized glycosaminoglycans, oxidized ribonucleic acids, oxidized biological cells, oxidized N-terminal serine residues of proteins, and oxidized N-terminal threonine residues of proteins.

* * * * *